(12) United States Patent
Hendricksen et al.

(10) Patent No.: US 9,211,119 B2
(45) Date of Patent: Dec. 15, 2015

(54) SUTURE PASSERS AND METHODS OF PASSING SUTURE

(71) Applicant: Ceterix Orthopaedics, Inc., Menlo Park, CA (US)

(72) Inventors: Michael J. Hendricksen, Redwood City, CA (US); Justin D. Saliman, Los Angeles, CA (US); Yoav Ben-Haim, San Francisco, CA (US); Mark Y. Hirotsuka, San Jose, CA (US); Michael Murillo, Menlo Park, CA (US); Christopher P. Bender, Oakland, CA (US)

(73) Assignee: Ceterix Orthopaedics, Inc., Menlo Park, CA (US)

( * ) Notice: Subject to any disclaimer, the term of this patent is extended or adjusted under 35 U.S.C. 154(b) by 344 days.

(21) Appl. No.: 13/844,252

(22) Filed: Mar. 15, 2013

(65) Prior Publication Data

US 2014/0276981 A1 Sep. 18, 2014

(51) Int. Cl.
*A61B 17/04* (2006.01)

(52) U.S. Cl.
CPC .......... *A61B 17/0483* (2013.01); *A61B 17/0469* (2013.01); *A61B 17/0482* (2013.01)

(58) Field of Classification Search
CPC ........... A61B 17/0469; A61B 17/0482; A61B 17/0483
See application file for complete search history.

(56) References Cited

U.S. PATENT DOCUMENTS

| | | | |
|---|---|---|---|
| 1,037,864 | A | 9/1912 | Carlson et al. |
| 2,738,790 | A | 3/1956 | Todt, Sr. et al. |
| 2,748,773 | A | 6/1956 | Vacheresse, Jr. |
| 3,470,875 | A | 10/1969 | Johnson |
| 3,580,256 | A | 5/1971 | Wilkinson et al. |
| 3,807,407 | A | 4/1974 | Schweizer |
| 3,842,840 | A | 10/1974 | Schweizer |
| 3,901,244 | A | 8/1975 | Schweizer |
| 4,021,896 | A | 5/1977 | Stierlein |
| 4,109,658 | A | 8/1978 | Hughes |
| 4,164,225 | A | 8/1979 | Johnson et al. |
| 4,236,470 | A | 12/1980 | Stenson |
| 4,345,601 | A | 8/1982 | Fukuda |
| 4,440,171 | A | 4/1984 | Nomoto et al. |
| 4,553,543 | A | 11/1985 | Amarasinghe |
| 4,605,002 | A | 8/1986 | Rebuffat |

(Continued)

FOREIGN PATENT DOCUMENTS

| | | |
|---|---|---|
| CN | 201263696 Y | 7/2009 |
| CN | 101961256 A | 2/2011 |

(Continued)

OTHER PUBLICATIONS

Murillo et al.; U.S. Appl. No. 14/572,485 entitled "Automatically reloading suture passer devices and methods," filed Dec. 16, 2014.

(Continued)

*Primary Examiner* — Ryan Severson
(74) *Attorney, Agent, or Firm* — Shay Glenn LLP

(57) ABSTRACT

Suture passer devices, including suture passers configured with an axially slideable jaw that includes a tissue-penetrating distal end region. Also described are suture passers including jaws housing tissue penetrating needles to pass suture that are substantially thin. Methods of using such devices to pass a suture through tissue are provided.

18 Claims, 38 Drawing Sheets

(56) References Cited

U.S. PATENT DOCUMENTS

| | | |
|---|---|---|
| 4,706,666 A | 11/1987 | Sheets |
| 4,836,205 A | 6/1989 | Barrett |
| 4,957,498 A | 9/1990 | Caspari et al. |
| 4,981,149 A | 1/1991 | Yoon et al. |
| 5,002,561 A | 3/1991 | Fisher |
| 5,011,491 A | 4/1991 | Boenko et al. |
| 5,037,433 A | 8/1991 | Wilk et al. |
| 5,059,201 A | 10/1991 | Asnis |
| 5,112,344 A | 5/1992 | Petros |
| 5,129,912 A | 7/1992 | Noda et al. |
| 5,156,608 A | 10/1992 | Troidl et al. |
| 5,193,473 A | 3/1993 | Asao et al. |
| 5,219,358 A | 6/1993 | Bendel et al. |
| 5,222,962 A | 6/1993 | Burkhart |
| 5,250,053 A | 10/1993 | Snyder |
| 5,250,055 A | 10/1993 | Moore et al. |
| 5,281,237 A | 1/1994 | Gimpelson |
| 5,312,422 A | 5/1994 | Trott |
| 5,330,488 A | 7/1994 | Goldrath |
| 5,336,229 A | 8/1994 | Noda |
| 5,342,389 A | 8/1994 | Haber et al. |
| 5,364,410 A | 11/1994 | Failla et al. |
| 5,368,601 A | 11/1994 | Sauer et al. |
| 5,389,103 A | 2/1995 | Melzer et al. |
| 5,391,174 A | 2/1995 | Weston |
| 5,397,325 A | 3/1995 | Della Badia et al. |
| 5,403,328 A | 4/1995 | Shallman |
| 5,405,352 A | 4/1995 | Weston |
| 5,405,532 A | 4/1995 | Loew et al. |
| 5,431,666 A | 7/1995 | Sauer et al. |
| 5,437,681 A | 8/1995 | Meade et al. |
| 5,454,823 A | 10/1995 | Richardson et al. |
| 5,454,834 A | 10/1995 | Boebel et al. |
| 5,468,251 A | 11/1995 | Buelna |
| 5,474,057 A | 12/1995 | Makower et al. |
| 5,478,344 A | 12/1995 | Stone et al. |
| 5,478,345 A | 12/1995 | Stone et al. |
| 5,480,406 A | 1/1996 | Nolan et al. |
| 5,496,335 A | 3/1996 | Thomason et al. |
| 5,499,991 A | 3/1996 | Garman et al. |
| 5,507,757 A | 4/1996 | Sauer et al. |
| 5,520,702 A | 5/1996 | Sauer et al. |
| 5,540,704 A | 7/1996 | Gordon et al. |
| 5,540,705 A | 7/1996 | Meade et al. |
| 5,562,686 A | 10/1996 | Sauer et al. |
| 5,569,301 A | 10/1996 | Granger et al. |
| 5,571,090 A | 11/1996 | Sherts |
| 5,571,119 A | 11/1996 | Atala |
| 5,575,800 A | 11/1996 | Gordon |
| 5,578,044 A | 11/1996 | Gordon et al. |
| 5,601,576 A | 2/1997 | Garrison |
| 5,607,435 A | 3/1997 | Sachdeva et al. |
| 5,616,131 A | 4/1997 | Sauer et al. |
| 5,618,290 A | 4/1997 | Toy et al. |
| 5,626,588 A | 5/1997 | Sauer et al. |
| 5,632,751 A | 5/1997 | Piraka |
| 5,643,289 A | 7/1997 | Sauer et al. |
| 5,645,552 A | 7/1997 | Sherts |
| 5,653,716 A | 8/1997 | Malo et al. |
| 5,665,096 A | 9/1997 | Yoon |
| 5,669,917 A | 9/1997 | Sauer et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,713,910 A | 2/1998 | Gordon et al. |
| 5,728,107 A | 3/1998 | Zlock et al. |
| 5,728,113 A | 3/1998 | Sherts |
| 5,730,747 A | 3/1998 | Ek et al. |
| 5,741,278 A | 4/1998 | Stevens |
| 5,749,879 A | 5/1998 | Middleman et al. |
| 5,755,728 A | 5/1998 | Maki |
| 5,759,188 A | 6/1998 | Yoon |
| 5,766,183 A | 6/1998 | Sauer |
| 5,792,153 A | 8/1998 | Swain et al. |
| 5,800,445 A | 9/1998 | Ratcliff et al. |
| 5,814,054 A | 9/1998 | Kortenbach et al. |
| 5,824,009 A | 10/1998 | Fukuda et al. |
| 5,827,300 A | 10/1998 | Fleega |
| 5,843,126 A | 12/1998 | Jameel |
| 5,865,836 A | 2/1999 | Miller |
| 5,871,490 A | 2/1999 | Schulze et al. |
| 5,876,411 A | 3/1999 | Kontos |
| 5,876,412 A | 3/1999 | Piraka |
| 5,895,393 A | 4/1999 | Pagedas |
| 5,895,395 A | 4/1999 | Yeung |
| 5,897,563 A | 4/1999 | Yoon et al. |
| 5,899,911 A | 5/1999 | Carter |
| 5,906,630 A | 5/1999 | Anderhub et al. |
| 5,908,428 A | 6/1999 | Scirica et al. |
| 5,935,138 A | 8/1999 | McJames, II et al. |
| 5,938,668 A | 8/1999 | Scirica et al. |
| 5,944,739 A | 8/1999 | Zlock et al. |
| 5,947,982 A | 9/1999 | Duran |
| 5,980,538 A | 11/1999 | Fuchs et al. |
| 5,993,466 A | 11/1999 | Yoon |
| 6,042,601 A | 3/2000 | Smith |
| 6,048,351 A | 4/2000 | Gordon et al. |
| 6,051,006 A | 4/2000 | Shluzas et al. |
| 6,053,933 A | 4/2000 | Balazs et al. |
| 6,056,771 A | 5/2000 | Proto |
| 6,071,289 A | 6/2000 | Stefanchik et al. |
| 6,077,276 A | 6/2000 | Kontos |
| 6,099,550 A | 8/2000 | Yoon |
| 6,113,610 A | 9/2000 | Poncet |
| 6,126,666 A | 10/2000 | Trapp et al. |
| 6,129,741 A | 10/2000 | Wurster et al. |
| 6,139,556 A | 10/2000 | Kontos |
| 6,152,934 A | 11/2000 | Harper et al. |
| 6,159,224 A | 12/2000 | Yoon |
| 6,190,396 B1 | 2/2001 | Whitin et al. |
| 6,221,085 B1 | 4/2001 | Djurovic |
| 6,238,414 B1 | 5/2001 | Griffiths |
| 6,264,694 B1 | 7/2001 | Weiler |
| 6,277,132 B1 | 8/2001 | Brhel |
| 6,322,570 B1 | 11/2001 | Matsutani et al. |
| 6,325,808 B1 | 12/2001 | Bernard et al. |
| 6,355,050 B1 | 3/2002 | Andreas et al. |
| 6,368,334 B1 | 4/2002 | Sauer |
| 6,443,963 B1 | 9/2002 | Baldwin et al. |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,585,744 B1 | 7/2003 | Griffith |
| 6,626,917 B1 | 9/2003 | Craig |
| 6,626,929 B1 | 9/2003 | Bannerman |
| 6,638,283 B2 | 10/2003 | Thal |
| 6,638,286 B1 | 10/2003 | Burbank et al. |
| 6,641,592 B1 | 11/2003 | Sauer et al. |
| 6,719,765 B2 | 4/2004 | Bonutti |
| 6,723,107 B1 | 4/2004 | Skiba et al. |
| 6,770,084 B1 | 8/2004 | Bain et al. |
| 6,896,686 B2 | 5/2005 | Weber |
| 6,921,408 B2 | 7/2005 | Sauer |
| 6,923,806 B2 | 8/2005 | Hooven et al. |
| 6,923,819 B2 | 8/2005 | Meade et al. |
| 6,936,054 B2 | 8/2005 | Chu |
| 6,984,237 B2 | 1/2006 | Hatch et al. |
| 6,991,635 B2 | 1/2006 | Takamoto et al. |
| 6,997,931 B2 | 2/2006 | Sauer et al. |
| 6,997,932 B2 | 2/2006 | Dreyfuss et al. |
| 7,004,951 B2 | 2/2006 | Gibbens, III |
| 7,029,480 B2 | 4/2006 | Klein et al. |
| 7,029,481 B1 | 4/2006 | Burdulis, Jr. et al. |
| 7,041,111 B2 | 5/2006 | Chu |
| 7,063,710 B2 | 6/2006 | Takamoto et al. |
| 7,087,060 B2 | 8/2006 | Clark |
| 7,112,208 B2 | 9/2006 | Morris et al. |
| 7,118,583 B2 | 10/2006 | O'Quinn et al. |
| 7,131,978 B2 | 11/2006 | Sancoff et al. |
| 7,166,116 B2 | 1/2007 | Lizardi et al. |
| 7,175,636 B2 | 2/2007 | Yamamoto et al. |
| 7,211,093 B2 | 5/2007 | Sauer et al. |

(56) References Cited

U.S. PATENT DOCUMENTS

| | | |
|---|---|---|
| 7,232,448 B2 | 6/2007 | Battles et al. |
| 7,235,086 B2 | 6/2007 | Sauer et al. |
| 7,311,715 B2 | 12/2007 | Sauer et al. |
| 7,344,545 B2 | 3/2008 | Takemoto et al. |
| 7,390,328 B2 | 6/2008 | Modesitt |
| 7,481,817 B2 | 1/2009 | Sauer |
| 7,491,212 B2 | 2/2009 | Sikora et al. |
| 7,588,583 B2 | 9/2009 | Hamilton et al. |
| 7,594,922 B1 | 9/2009 | Goble et al. |
| 7,632,284 B2 | 12/2009 | Martinek et al. |
| 7,674,276 B2 | 3/2010 | Stone et al. |
| 7,722,630 B1 | 5/2010 | Stone et al. |
| 7,731,727 B2 | 6/2010 | Sauer |
| 7,736,372 B2 | 6/2010 | Reydel et al. |
| 7,749,236 B2 | 7/2010 | Oberlaender et al. |
| 7,842,050 B2 | 11/2010 | Diduch et al. |
| 7,879,046 B2 | 2/2011 | Weinert et al. |
| 7,883,519 B2 | 2/2011 | Oren et al. |
| 7,951,147 B2 | 5/2011 | Privitera et al. |
| 7,951,159 B2 | 5/2011 | Stokes et al. |
| 7,972,344 B2 | 7/2011 | Murray et al. |
| 8,394,112 B2 | 3/2013 | Nason |
| 8,398,673 B2 | 3/2013 | Hinchliffe et al. |
| 8,449,533 B2 | 5/2013 | Saliman et al. |
| 8,465,505 B2 | 6/2013 | Murillo et al. |
| 2003/0023250 A1 | 1/2003 | Watschke et al. |
| 2003/0065336 A1 | 4/2003 | Xiao |
| 2003/0065337 A1 | 4/2003 | Topper et al. |
| 2003/0078599 A1 | 4/2003 | O'Quinn et al. |
| 2003/0204194 A1 | 10/2003 | Bittar |
| 2003/0216755 A1 | 11/2003 | Shikhman et al. |
| 2003/0233106 A1 | 12/2003 | Dreyfuss |
| 2004/0249392 A1 | 12/2004 | Mikkaichi et al. |
| 2004/0249394 A1 | 12/2004 | Morris et al. |
| 2004/0267304 A1 | 12/2004 | Zannis et al. |
| 2005/0033319 A1 | 2/2005 | Gambale et al. |
| 2005/0033365 A1 | 2/2005 | Courage |
| 2005/0080434 A1 | 4/2005 | Chung et al. |
| 2005/0090837 A1 | 4/2005 | Sixto, Jr. et al. |
| 2005/0090840 A1 | 4/2005 | Gerbino et al. |
| 2005/0154403 A1 | 7/2005 | Sauer et al. |
| 2005/0228406 A1 | 10/2005 | Bose |
| 2005/0288690 A1 | 12/2005 | Bourque et al. |
| 2006/0020272 A1 | 1/2006 | Gildenberg |
| 2006/0047289 A1 | 3/2006 | Fogel |
| 2006/0084974 A1 | 4/2006 | Privitera et al. |
| 2006/0282098 A1 | 12/2006 | Shelton et al. |
| 2007/0032799 A1 | 2/2007 | Pantages et al. |
| 2007/0219571 A1 | 9/2007 | Balbierz et al. |
| 2007/0250118 A1 | 10/2007 | Masini |
| 2007/0260260 A1 | 11/2007 | Hahn et al. |
| 2007/0260278 A1 | 11/2007 | Wheeler et al. |
| 2008/0086147 A1 | 4/2008 | Knapp |
| 2008/0091219 A1 | 4/2008 | Marshall et al. |
| 2008/0097489 A1 | 4/2008 | Goldfarb et al. |
| 2008/0140091 A1 | 6/2008 | DeDeyne et al. |
| 2008/0228204 A1 | 9/2008 | Hamilton et al. |
| 2008/0234725 A1 | 9/2008 | Griffiths et al. |
| 2008/0243147 A1 | 10/2008 | Hamilton et al. |
| 2008/0269783 A1 | 10/2008 | Griffith |
| 2008/0294256 A1 | 11/2008 | Hagan et al. |
| 2009/0012538 A1 | 1/2009 | Saliman |
| 2009/0018554 A1 | 1/2009 | Thorne et al. |
| 2009/0062816 A1 | 3/2009 | Weber |
| 2009/0062819 A1 | 3/2009 | Burkhart et al. |
| 2009/0105751 A1 | 4/2009 | Zentgraf |
| 2009/0131956 A1 | 5/2009 | Dewey et al. |
| 2009/0209998 A1 | 8/2009 | Widmann |
| 2009/0216268 A1 | 8/2009 | Panter |
| 2009/0228041 A1 | 9/2009 | Domingo |
| 2009/0259233 A1 | 10/2009 | Bogart et al. |
| 2009/0281619 A1 | 11/2009 | Le et al. |
| 2009/0306684 A1 | 12/2009 | Stone et al. |
| 2009/0306776 A1 | 12/2009 | Murray |
| 2010/0057109 A1 | 3/2010 | Clerc et al. |
| 2010/0106169 A1 | 4/2010 | Niese et al. |
| 2010/0114137 A1 | 5/2010 | Vidal et al. |
| 2010/0121352 A1 | 5/2010 | Murray et al. |
| 2010/0130990 A1 | 5/2010 | Saliman |
| 2010/0145364 A1 | 6/2010 | Keren et al. |
| 2010/0185232 A1 | 7/2010 | Hughett et al. |
| 2010/0198235 A1 | 8/2010 | Pierce et al. |
| 2010/0228271 A1 | 9/2010 | Marshall et al. |
| 2010/0241142 A1 | 9/2010 | Akyuz et al. |
| 2010/0249809 A1 | 9/2010 | Singhatat et al. |
| 2010/0280530 A1 | 11/2010 | Hashiba |
| 2010/0305581 A1 | 12/2010 | Hart |
| 2010/0305583 A1 | 12/2010 | Baird et al. |
| 2010/0331863 A2 | 12/2010 | Saliman |
| 2011/0022063 A1 | 1/2011 | McClurg et al. |
| 2011/0028998 A1 | 2/2011 | Adams et al. |
| 2011/0060350 A1 | 3/2011 | Powers et al. |
| 2011/0087246 A1 | 4/2011 | Saliman et al. |
| 2011/0112555 A1 | 5/2011 | Overes et al. |
| 2011/0112556 A1 | 5/2011 | Saliman |
| 2011/0118760 A1 | 5/2011 | Gregoire et al. |
| 2011/0130773 A1 | 6/2011 | Saliman et al. |
| 2011/0152892 A1 | 6/2011 | Saliman et al. |
| 2011/0190815 A1 | 8/2011 | Saliman |
| 2011/0218557 A1 | 9/2011 | Saliman |
| 2011/0251626 A1 | 10/2011 | Wyman et al. |
| 2011/0270280 A1 | 11/2011 | Saliman |
| 2012/0179254 A1 | 7/2012 | Saliman |
| 2012/0239062 A1 | 9/2012 | Saliman et al. |
| 2012/0283750 A1 | 11/2012 | Saliman et al. |
| 2012/0283753 A1 | 11/2012 | Saliman et al. |
| 2012/0303046 A1 | 11/2012 | Stone et al. |
| 2013/0072948 A1 | 3/2013 | States, III et al. |
| 2013/0238040 A1 | 9/2013 | Saliman et al. |
| 2013/0253647 A1 | 9/2013 | Saliman et al. |
| 2014/0188136 A1 | 7/2014 | Cournoyer et al. |

FOREIGN PATENT DOCUMENTS

| | | |
|---|---|---|
| EP | 0647431 A2 | 4/1995 |
| JP | 3032847 U | 3/1991 |
| JP | 2009138029 A | 6/2009 |
| JP | 2009538190 | 11/2009 |
| SU | 376089 A | 4/1973 |
| SU | 7288848 A1 | 4/1980 |
| SU | 1725847 A1 | 4/1992 |
| WO | WO 92/05828 A1 | 4/1992 |
| WO | WO 95/13021 A1 | 5/1995 |
| WO | WO 98/31288 A1 | 7/1998 |
| WO | WO 99/34744 A1 | 7/1999 |
| WO | WO 99/42036 A1 | 8/1999 |
| WO | WO 99/47050 A2 | 9/1999 |
| WO | WO01/56478 A1 | 8/2001 |
| WO | WO 02/07607 A1 | 1/2002 |
| WO | WO 02/096296 A1 | 12/2002 |
| WO | WO 03/077771 A1 | 9/2003 |
| WO | WO 2006/001040 A1 | 1/2006 |
| WO | WO 2006/040562 A1 | 4/2006 |
| WO | WO 2010/141695 A1 | 12/2010 |
| WO | WO 2011/057245 A2 | 5/2011 |

OTHER PUBLICATIONS

Saliman et al.; U.S. Appl. No. 14/546,942 entitled "Suture passer and method for hip labrum repair," filed Nov. 18, 2014.

George et al.; U.S. Appl. No. 14/608,057 entitled "Arthroscopic knot pusher and suture cutter," filed Jan. 28, 2015.

Hendricksen et al.; U.S. Appl. No. 14/265,848 entitled "Suture passer with radiused upper jaw," filed Apr. 30, 2014.

Saliman et al.; U.S. Appl. No. 14/451,293 entitled "Transosteal anchoring methods for tissue repair," filed Aug. 4, 2014.

George et al.; U.S. Appl. No. 14/494,561 entitled "Arthroscopic knot pusher and suture cutter," filed Sep. 23, 2014.

Duerig, T. et al., "An overview of nitinol medical applications" Materials Science and Engineering A273-275, May 1999.

Murillo et al.; U.S. Appl. No. 13/893,154 entitled "Suture passer devices and methods," filed May 13, 2013.

(56) References Cited

OTHER PUBLICATIONS

Saliman; U.S. Appl. No. 14/292,695 entitled "Suture methods for forming locking loops stitches," filed May 30, 2014.

Nord et al.; Posterior lateral meniscal root tears and meniscal repair; Orthopedics Today; 5 pgs; Nov. 2010; retrieved from the internet on Aug. 21, 2014 (http://www.healio.com/orthopedics/arthroscopy/news/print/orthopedics-today/%7B1b52a700-e986-4524-ac7d-6043c9799e15%7D/posterior-lateral-meniscal-root-tears-and-meniscal-repair).

Asik et al.; Strength of different meniscus suturing techniques; Knee Sur, Sports Traumotol, Arthroscopy; vol. 5; No. 2; pp. 80-83; (year of publication is sufficiently earlier than the effective U.S. filing date and any foreign priority date) 1997.

Asik et al.; Failure strength of repair devices versus meniscus suturing techniques; Knee Surg, Sports Traumatol, Arthrosc; vol. 10; No. 1; pp. 25-29; Jan. 2002.

Arthrex®, Arthrex, Inc., "The Next Generation in Shoulder Repair Technology," Product Brochure from Arthrex, Inc; Naples, Florida, (year of pub. sufficiently earlier than effective US filing date and any foreign priority date) 2007, 22 pages.

ArthroCare® Sportsmedicine, Sunnyvale, CA, SmartStitch® Suture Passing System with the PerfectPasser™, Product brochure, (year of pub. sufficiently earlier than effective US filing date and any foreign priority date) 2006, 4 pages.

BiPass(TM) Suture Punch, Biomet® Sports Medicine, Inc., accessed Feb. 29, 2008 at <http://www.arthrotek.com/prodpage.cfm?c=0A05&p=090706> 2 pages.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Cayenne Medical; CrossFix® II System (product webpage); 4 pgs.; downloaded Nov. 21, 2011 (www.cayennemedical.com/products/crossfix/).

Covidien Surgical; Endo Stitch 10 mm Suturing Device; accessed Dec. 4, 2012 at <http://www.autosuture.com/autosuture/pagebuilder.aspx?topicID=7407&breadcrumbs=0:63659,30691:0,309:0> 2pages.

Depuy Mitek, Inc; Raynham, MA, "Versalok Surgical Technique for Rotator Cuff Repair: The next generation in rotator cuff repair," Product brochure, (year of pub. sufficiently earlier than effective US filing date and any foreign priority date) 2007, 18 pages.

Linvatec Conmed Company, Largo, Florida, Product descriptions B17-19, B21; Tissue Repair Systems, Tissue Repair Accessories, and Master Arthroscopy Shoulder Instrument Set, (printed on or before Aug. 2007), 4 pages.

Ma et al; "Biomechanical Evaluation of Arthroscopic Rotator Cuff Stitches," J Bone Joint Surg Am, Jun. 2004; vol. 86(6):1211-1216.

Medsfera; Suturing devices; accessed Dec. 4, 2012 at <http://www.medsfera.ru/shiv.html> 13 pages.

Nho et al; "Biomechanical fixation in Arthroscopic Rotator Cuff Repair," Arthroscopy: J of Arthroscop and Related Surg; vol. 23. No. 1, Jan. 2007: pp. 94-102.

Rimmer et al.; Failure Strength of Different Meniscal Suturing Techniques; Arthroscopy: The Journal of Arthroscopic and Related Surgery; vol. 11; No. 2; pp. 146-150; Apr. 1995.

Schneeberger, et al; "Mechanical Strength of Arthroscopic Rotator Cuff Repair Techniques: An in Vitro Study," J Bone Joint Surg Am., Dec. 2002; 84:2152-2160.

Smith&Nephew; Fast-Fix Meniscal Repair System (product webpage); 4 pgs.; downloaded Nov. 21, 2011 (http://endo.smith-nephew.com/fr/node.asp?NodeId=3562).

Strobel; Manual of Arthroscopic Surgery (1st Edition); Springer Verlag, Hiedelberg © 2002; pp. 127-129; Dec. 15, 2001.

USS SportsMedicine ArthoSew™ Single Use Automated Suturing Device with 8.6 mm ArthroPort Cannula Set, Instructions for Use, <http:www.uss-sportsmed.com/imageServer.aspx?contentID=5020&contenttype=application/pdf> accessed Apr. 25, 2007, 2 pages.

USS SportsMedicine ArthroSew™ Suturing Device, <http://www.uss-sportsmed.com/SportsMedicine/pageBuilder.aspx?webPageID=0&topicID=7141&xsl=xsl/productPagePrint.xsl>, product description, accessed Apr. 25, 2007, 3 pages.

Hirotsuka et al.; U.S. Appl. No. 13/758,994 entitled "Pre-Tied Surgical Knots for Use With Suture Passers," filed Feb. 4, 2013.

McCutcheon et al.; U.S. Appl. No. 13/759,000 entitled "Methods and Devices for Preventing Tissue Bridging While Suturing," filed Feb. 4, 2013.

Saliman, J.; U.S. Appl. No. 13/759,006 entitled "Suture Passers," filed Feb. 4, 2013.

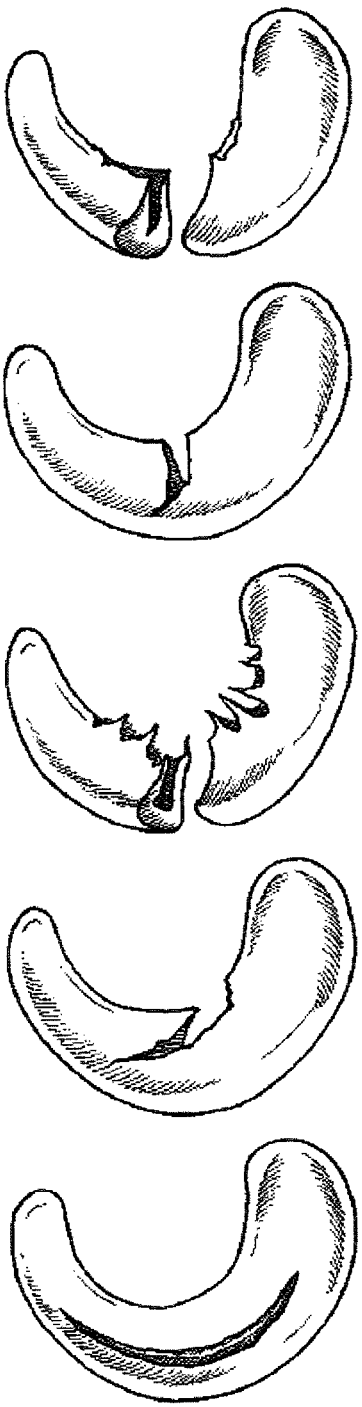
Tear patterns
FIG. 4A Vertical longitudinal
FIG. 4B Oblique
FIG. 4C Degenerative
FIG. 4D Transverse (Radial)
FIG. 4E Horizontal

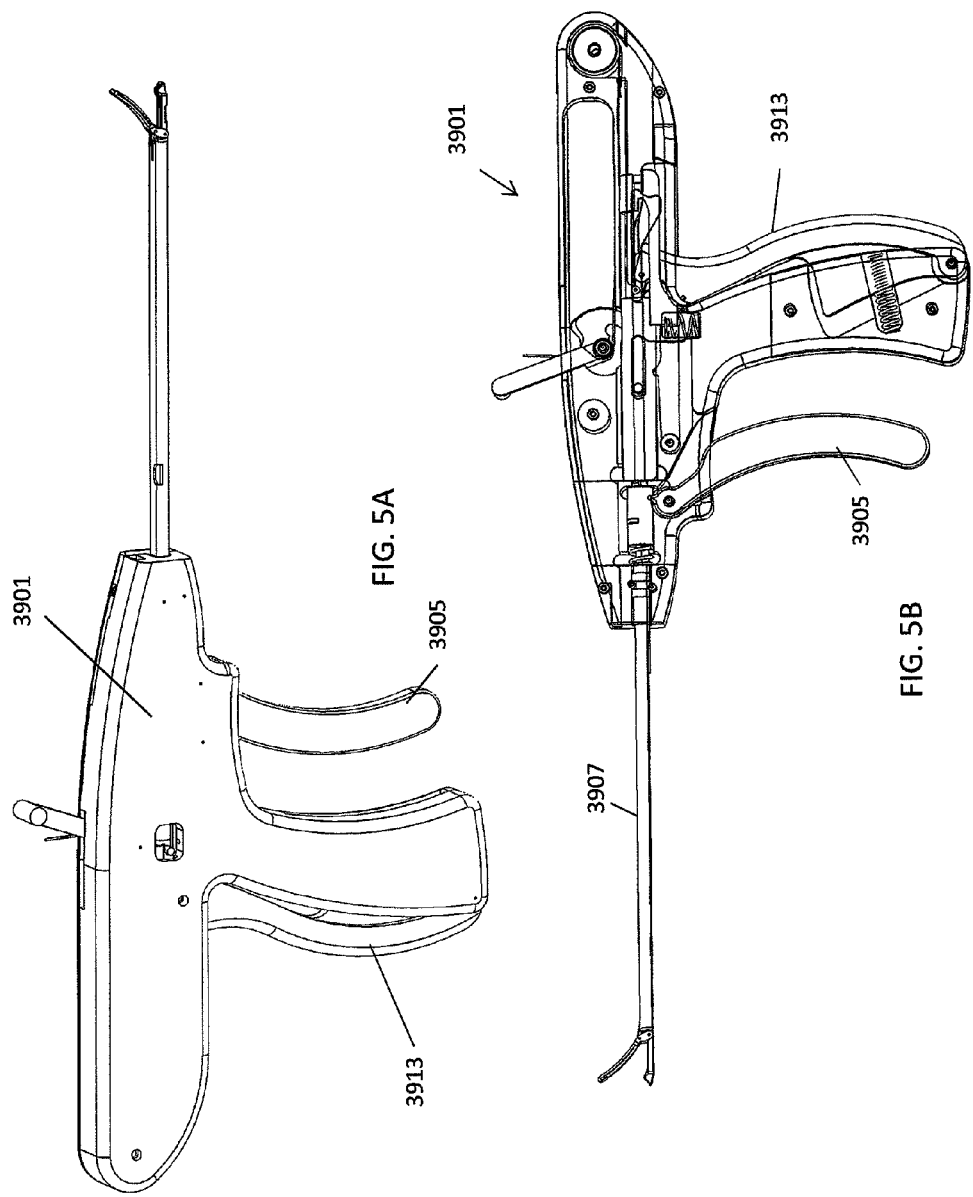

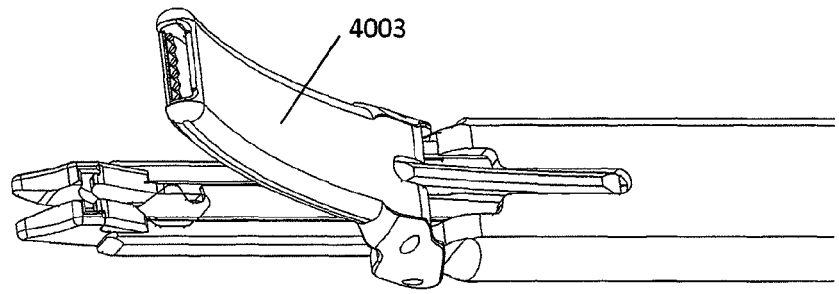
FIG. 6A
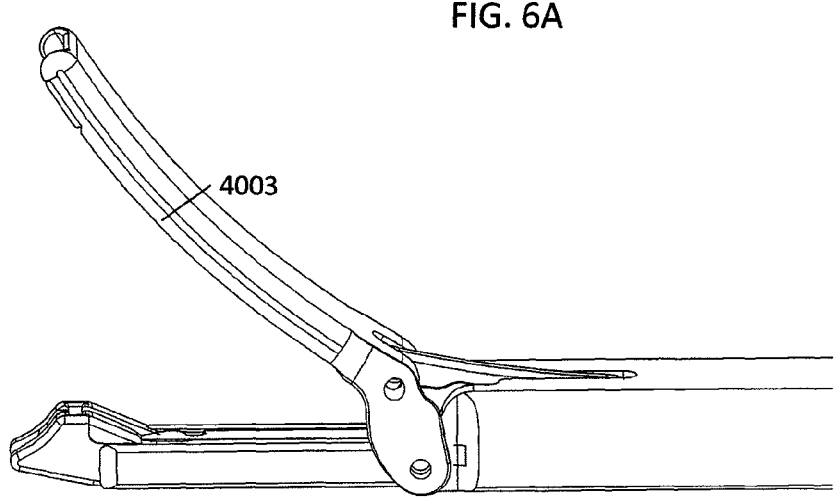
FIG. 6B
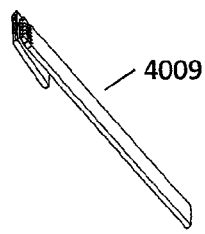
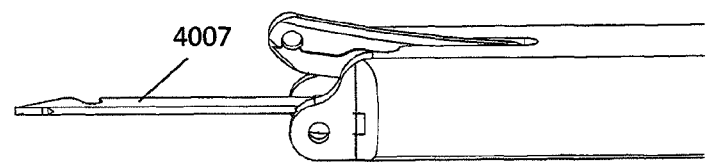
FIG. 6C

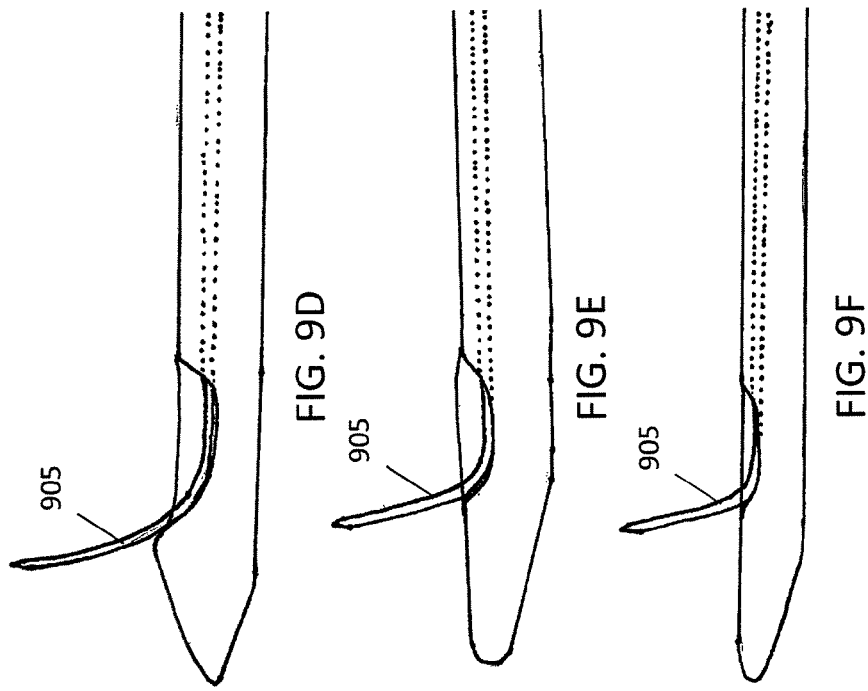
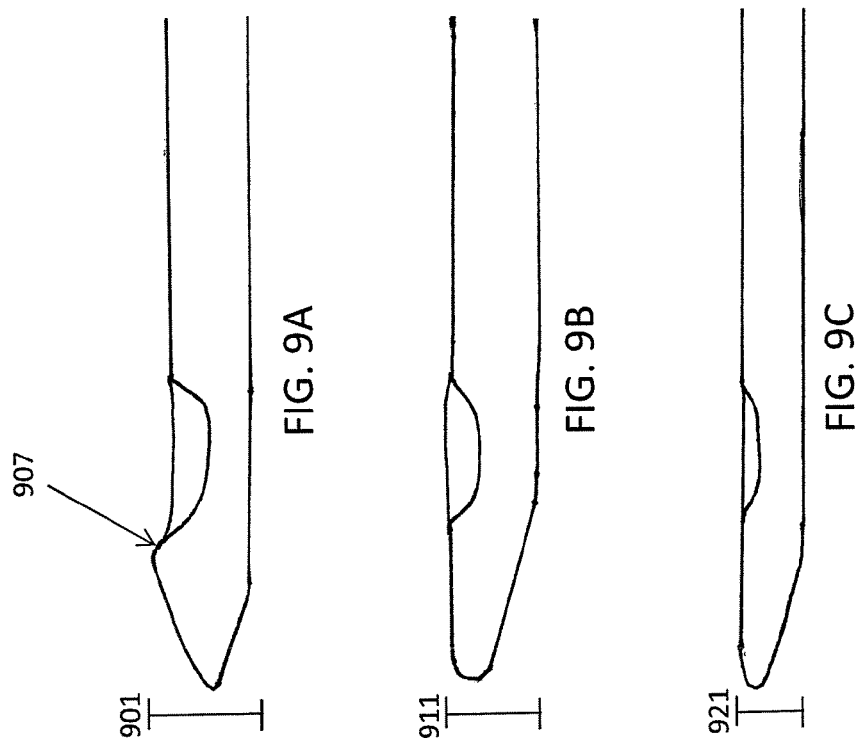

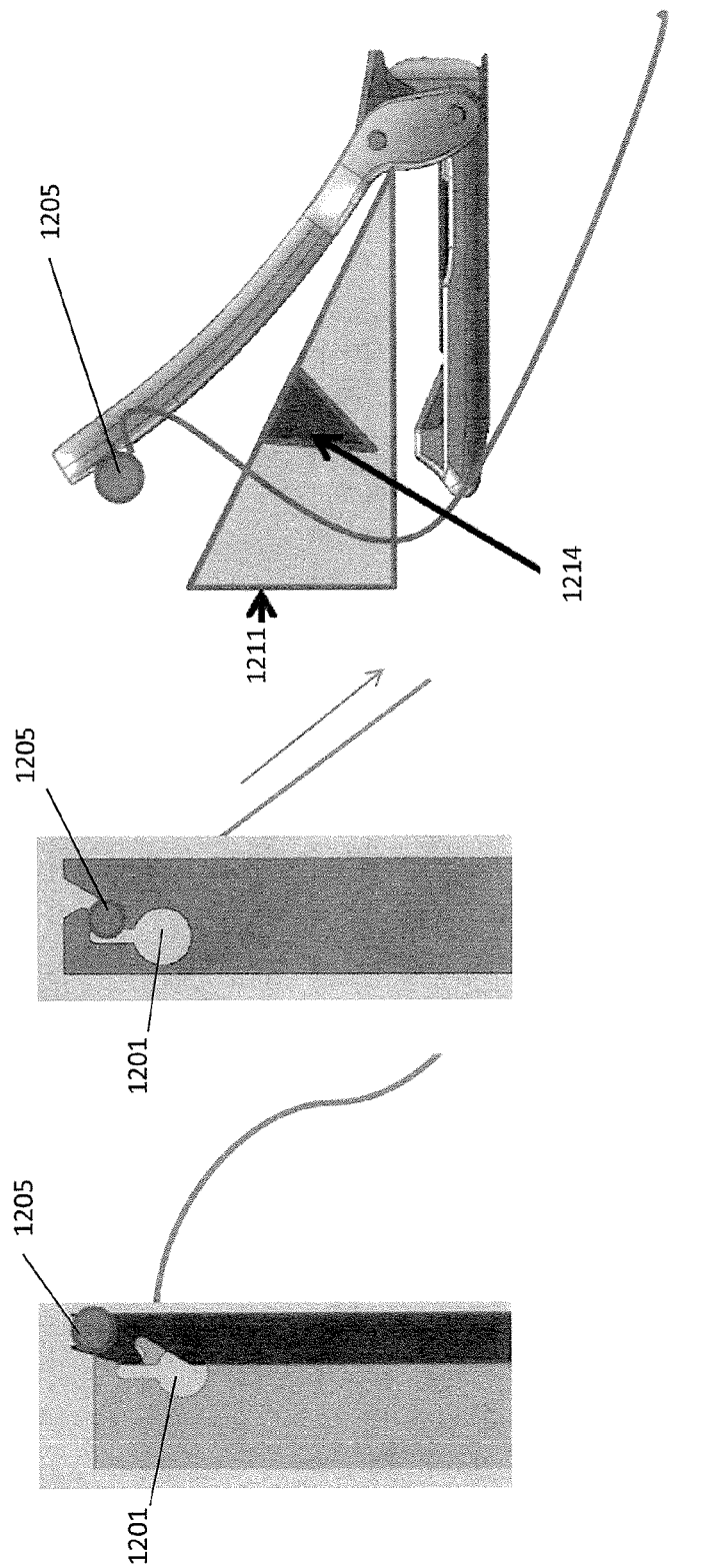

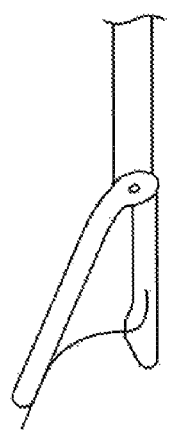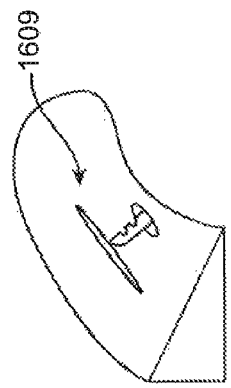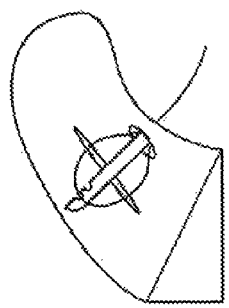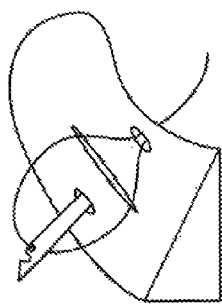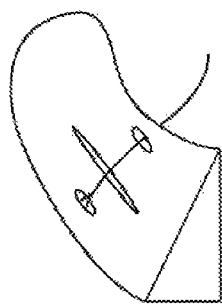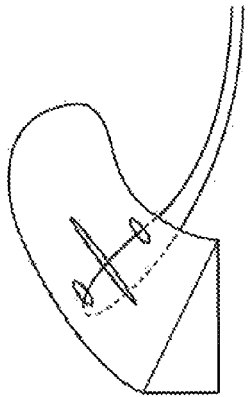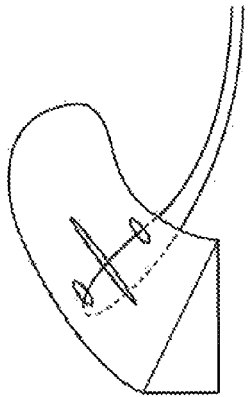

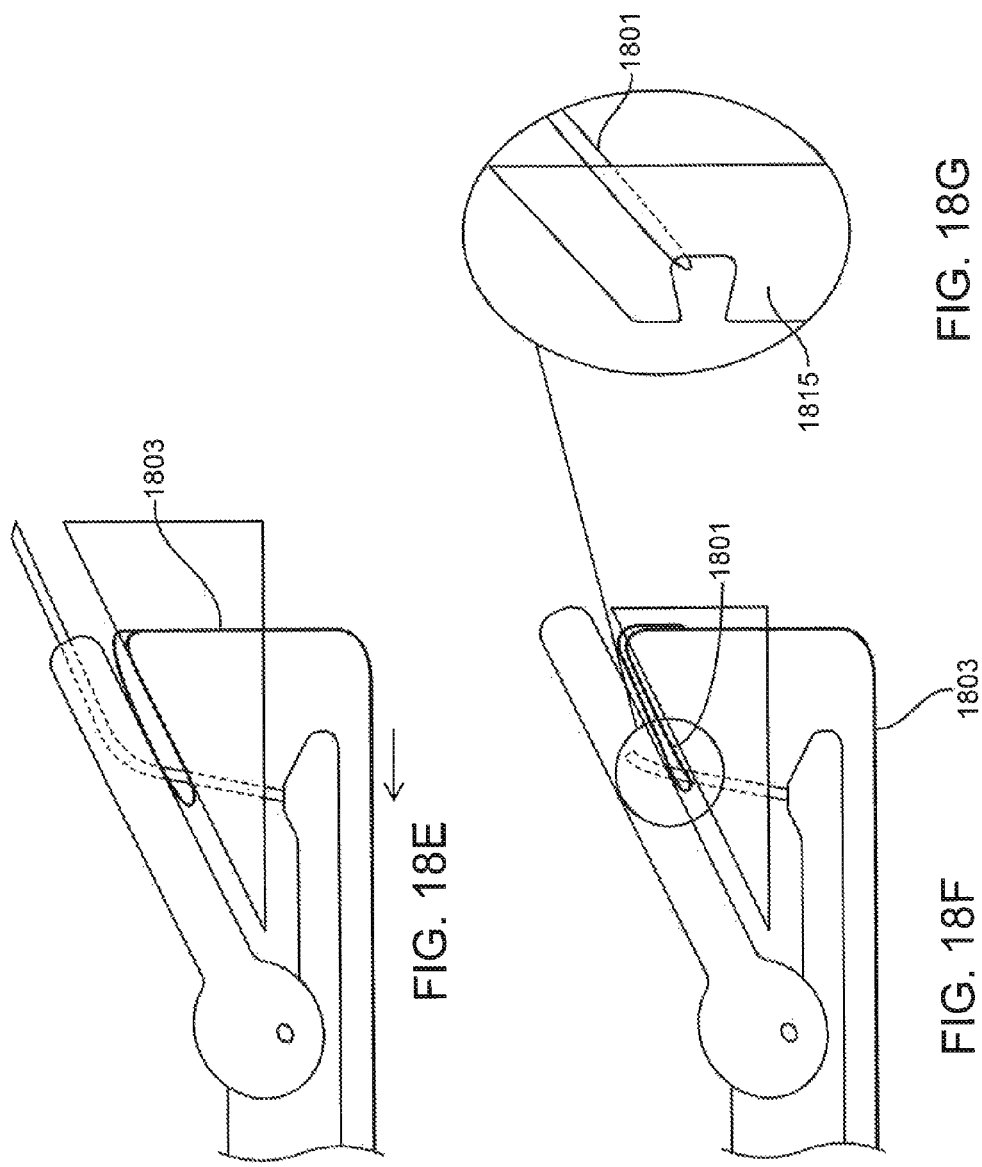

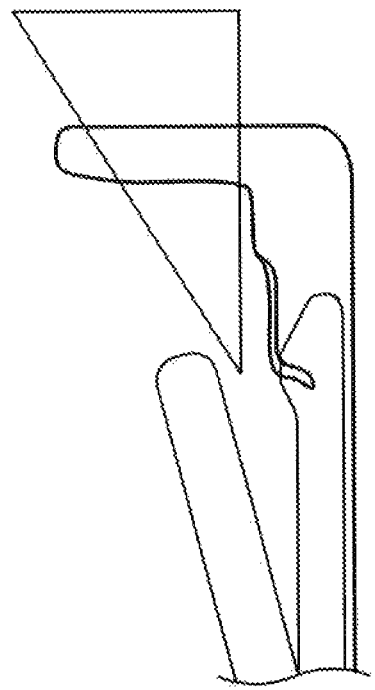
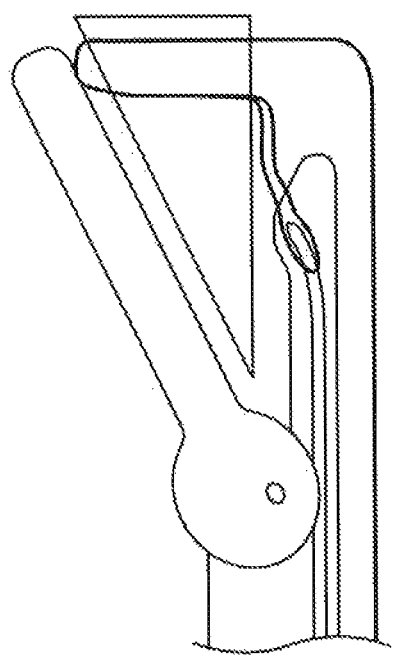
FIG. 18H
FIG. 18I

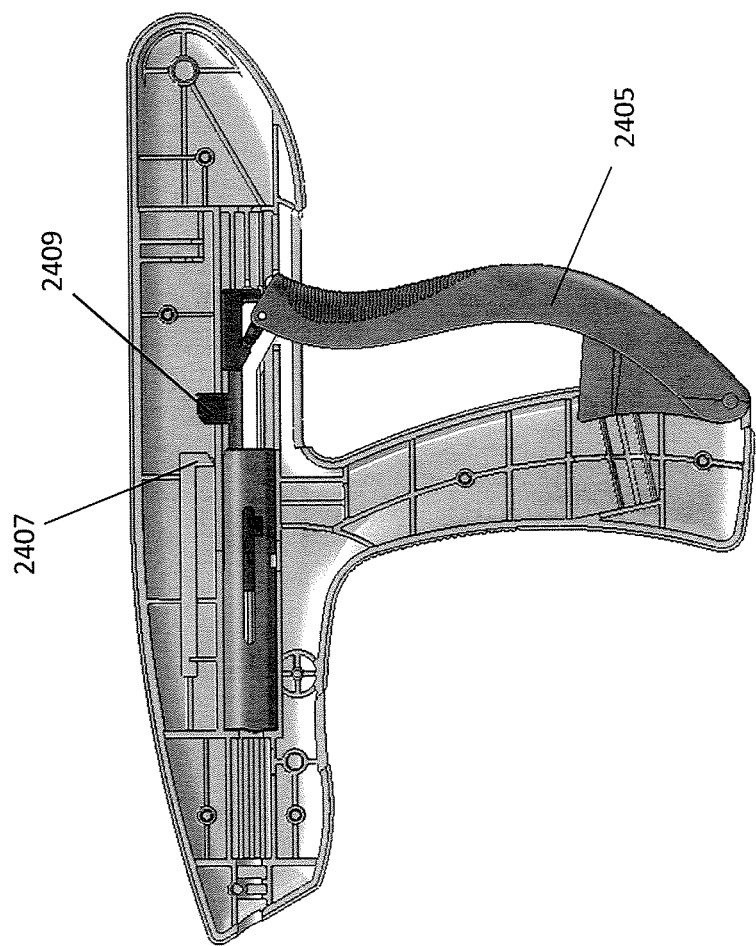

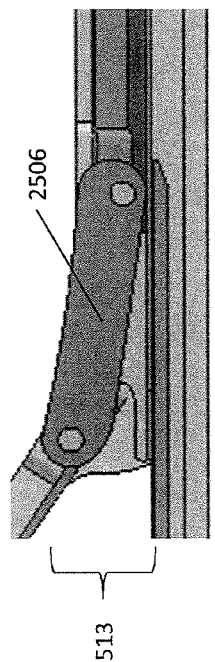
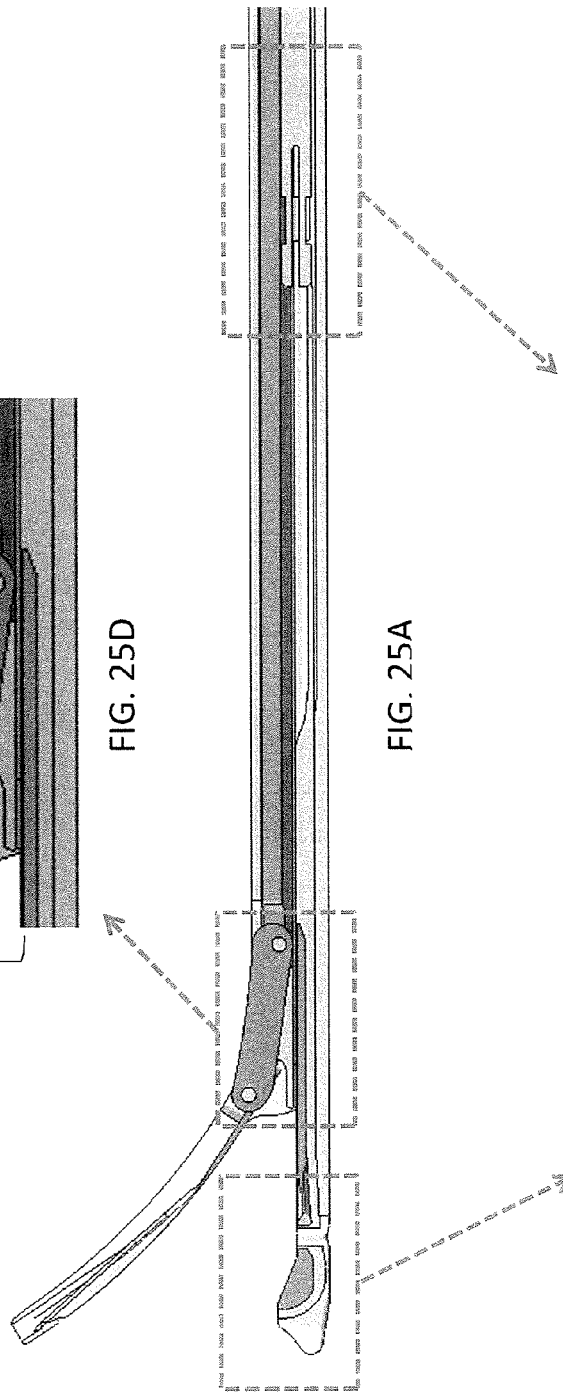
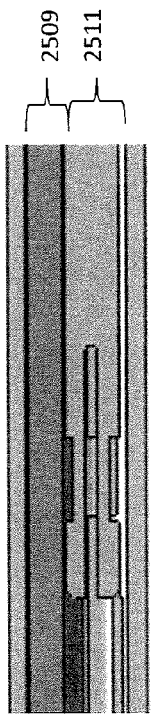
FIG. 25D
FIG. 25A
FIG. 25C
FIG. 25B

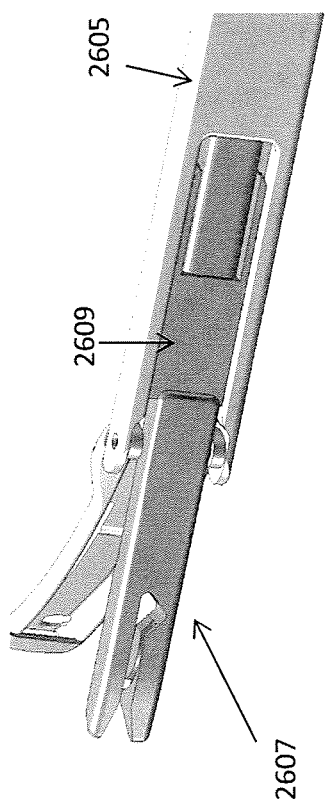
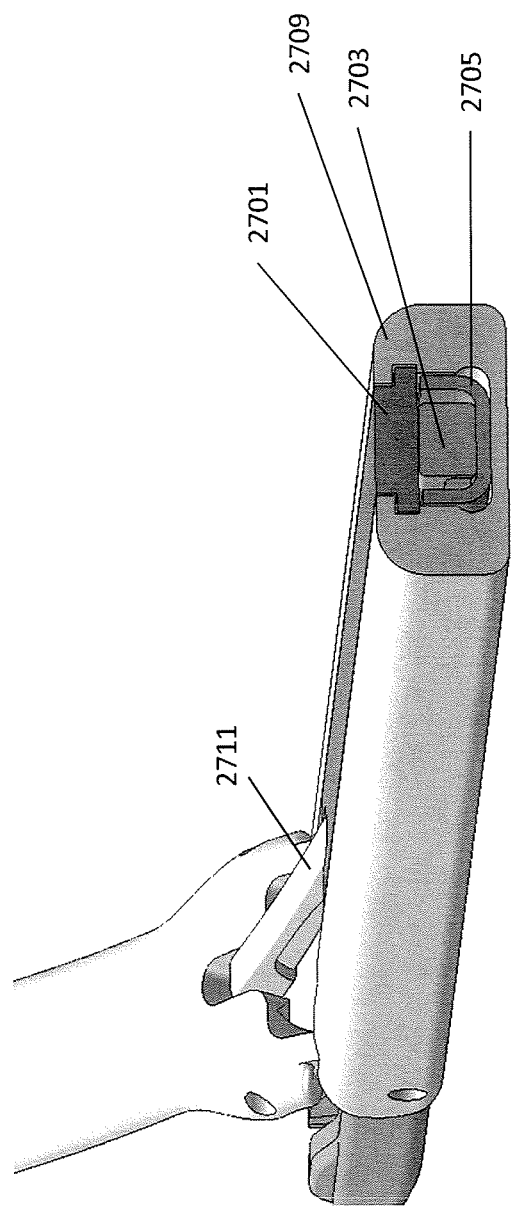

SUTURE PASSERS AND METHODS OF PASSING SUTURE

CROSS REFERENCE TO RELATED APPLICATIONS

This patent application does not claim priority to any other patent application.

The suture passers and methods of suturing described herein may related to, and may incorporate any of the features or elements described in the following patent applications, each of which is herein incorporated by reference in its entirety. Specifically: U.S. patent application Ser. No. 11/773,388, filed on Jul. 3, 2007, and titled "METHODS AND DEVICES FOR CONTINUOUS SUTURE PASSING"; U.S. patent application Ser. No. 12/972,222, filed on Dec. 17, 2010, and titled "METHODS AND DEVICES FOR CONTINUOUS SUTURE PASSING"; U.S. patent application Ser. No. 13/462,760, filed on May 2, 2012, and titled "METHODS OF MENISCUS REPAIR"; U.S. patent application Ser. No. 13/006,966, filed on Jan. 14, 2011, and titled "METHODS FOR CONTINUOUS SUTURE PASSING"; U.S. patent application Ser. No. 13/090,089, filed on Apr. 19, 2011, and titled "METHODS OF MENISCUS REPAIR"; U.S. patent application Ser. No. 12/291,159, filed on Nov. 5, 2008, and titled "SUTURE PASSING INSTRUMENT AND METHOD"; U.S. patent application Ser. No. 12/972,168, filed on Dec. 17, 2010, and titled "SUTURE PASSING INSTRUMENT AND METHOD"; U.S. patent application Ser. No. 13/062,664, filed on Apr. 19, 2011, and titled "KNOTLESS SUTURE ANCHORS"; U.S. patent application Ser. No. 12/620,029, filed on Nov. 17, 2009, and titled "METHODS OF SUTURING AND REPAIRING TISSUE USING A CONTINUOUS SUTURE PASSER DEVICE"; U.S. patent application Ser. No. 12/942,803, filed on Nov. 9, 2010, and titled "DEVICES, SYSTEMS AND METHODS FOR MENISCUS REPAIR"; U.S. patent application Ser. No. 13/462,728, filed on May 2, 2012, and titled "DEVICES, SYSTEMS AND METHODS FOR MENISCUS REPAIR"; U.S. patent application Ser. No. 13/114,983, filed on May 24, 2011, and titled "SUTURING AND REPAIRING TISSUE USING IN VIVO SUTURE LOADING"; U.S. patent application Ser. No. 13/347,184, filed on Jan. 10, 2012, and titled "IMPLANT AND METHOD FOR REPAIR OF THE ANTERIOR CRUCIATE LIGAMENT"; U.S. patent application Ser. No. 13/247,892, filed on Sep. 28, 2011, and titled "MENISCUS REPAIR"; U.S. patent application Ser. No. 13/323,391, filed on Dec. 12, 2011, and titled "SUTURE PASSER DEVICES AND METHODS"; and U.S. patent application Ser. No. 13/462,773, filed on May 2, 2012, and titled "SUTURE PASSER DEVICES AND METHODS".

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates to suture passers, suturing techniques, devices and methods, for surgical use and methods of repairing tissue. More particularly, described herein are suture passers that may be used for performing arthroscopic (including minimally invasive, e.g., endoscopic) procedures.

BACKGROUND

Suturing of tissue during surgical procedures is time consuming and can be particularly challenging in difficult to access body regions and regions that have limited clearance, such as regions partially surrounded or covered by bone. For many surgical procedures, it is necessary to make a large opening in the human body to expose the area requiring surgical repair. However, in many cases, accessing the tissue in this manner is undesirable, increasing recovery time, and exposing the patient to greater risk of infection.

Suturing instruments ("suture passers" or "suturing devices") have been developed to assist in accessing and treating internal body regions, and to generally assist a physician in repairing tissue. Although many such devices are available for endoscopic and/or percutaneous use, these devices suffer from a variety of problems, including limited ability to navigate and be operated within the tight confines of the body, risk of injury to adjacent structures, problems controlling the position and/or condition of the tissue before, during, and after passing the suture, as well as problems with the reliable functioning of the suture passer.

For example, some surgical instruments used in endoscopic procedures are limited by the manner in which they access the areas of the human body in need of repair. In particular, the instruments may not be able to access tissue or organs located deep within the body or that are in some way obstructed. In addition, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

For example, some variations of suture passers, such as those described in U.S. Pat. No. 7,377,926 to Taylor, have opposing jaws that open and close over tissue. One, or in some variations, both, jaws open, scissor-like, so that tissue may be inserted between the open jaws. Unfortunately, such devices cannot be adequately positioned for use in hard to navigate body regions such as the joints of the body, including the knee (e.g., meniscus) and the shoulder.

The meniscus is a C-shaped piece of fibrocartilage which is located at the peripheral aspect of the joint (e.g., the knee) between the condyles of the femur and the tibia on the lateral and medial sides of the knee. The central two-thirds of the meniscus has a limited blood supply while the peripheral one third typically has an excellent blood supply. Acute traumatic events commonly cause meniscus tears in younger patients while degenerative tears are more common in older patients as the menisci become increasingly brittle with age. Typically, when the meniscus is damaged, a torn piece of meniscus may move in an abnormal fashion inside the joint, which may lead to pain and loss of function of the joint. Early arthritis can also occur due to these tears as abnormal mechanical movement of torn meniscal tissue and the loss of the shock absorbing properties of the meniscus lead to destruction of the surrounding articular cartilage. Occasionally, it is possible to repair a torn meniscus. While this may be done arthroscopically, surgical repair using a suture has proven difficult to perform because of the hard-to-reach nature of the region and the difficulty in placing sutures in a way that compresses and secures the torn surfaces.

Arthroscopy typically involves inserting a fiberoptic telescope that is about the size of a pencil into the joint through an incision that is approximately ⅛ inch long. Fluid may then be inserted into the joint to distend the joint and to allow for visualization of the structures within that joint. Then, using miniature instruments which may be as small as 1/10 of an inch, the structures are examined and the surgery is performed.

The meniscus of the knee is just one example of a tissue that is difficult to access so that appropriate suturing may be performed. FIGS. 1A, 1B and 2 illustrate the anatomy of the meniscus in the context of a knee joint. As shown in FIG. 2 the capsule region (the outer edge region of the meniscus) is vascularized. Blood enters the meniscus from the menisculocapsular region 211 lateral to the meniscus. A typical meniscus has a flattened bottom (inferior surface or side) and a concave top (superior surface or side), and the outer cross-sectional shape is somewhat triangular. The outer edge of the meniscus transitions into the capsule. FIG. 3 illustrates the various fibers forming a meniscus. As illustrated in FIG. 3, there are circumferential fibers extending along the curved length of the meniscus, as well as radial fibers, and more randomly distributed mesh network fibers. Because of the relative orientations and structures of these fibers, and the predominance of circumferential fibers, it may be beneficial to repair the meniscus by suturing radially (vertically) rather than longitudinally or horizontally, depending on the type of repair being performed.

For example, FIGS. 4A-4E illustrate various tear patterns or injuries to a meniscus. Tears may be vertical/longitudinal (FIG. 4A), oblique (FIG. 4B), degenerative (FIG. 4C), including radially degenerative, transverse or radial (FIG. 4D) and horizontal (FIG. 4E). Most prior art devices for suturing or repairing the meniscus are only capable of reliably repairing vertical/longitudinal tears. Such devices are not typically useful for repairing radial or horizontal tears. Furthermore, prior art device mechanisms have a high inherent risk for iatrogenic injury to surrounding neurovascular structures and chondral surfaces.

Thus, there is a need for methods, devices and systems for suturing tissue, particularly tissue in difficult to access regions of the body including the joints (shoulder, knee, etc.). In particularly, it has proven useful to provide a device that may simply and reliably reach and pass sutures within otherwise inaccessible tissue regions. Such devices should be extremely low profile. Finally, it is useful to provide suturing devices that allow selective and specific penetration of the tissue by both the tissue penetrator (needle element) and a jaw so that complex (including right-angled) suturing patterns may be achieved. The methods, devices and systems described herein may address this need.

SUMMARY OF THE DISCLOSURE

The present invention relates to suture passers. In particular, described herein are suture passer devices having a bent or bendable first jaw extending from an elongate body, and a second jaw that is independently axially slideable relative to the elongate body (and/or first jaw) to form a distal-facing opening between the first and second jaws into which target tissue may be held and sutured by extending a tissue-penetrator (e.g., needle) between the first and second jaws. These devices may be configured to pass a suture multiple times through the tissue (e.g., passing both first and second ends of a suture) to create an entire loop of suture around a tissue such as a torn meniscus. Further, this device may be adapted for use with loops, snares, baskets and other suture passing aids. The devices described herein may be adapted to include an indicator (e.g., optical indicator) showing where the tissue penetrator (e.g., needle) of the suture passer will engage with the opposite (e.g., upper) jaw of the suture passer. In some variations, the suture passers describe herein are adapted so that the lower jaw moves axially both independently, e.g., to retract/extend for positioning around a target tissue, and in conjunction with closing of the jaws, e.g., upper jaw motion, around tissue so that the needle extending from the lower jaw contacts with the upper jaw in a predictable fashion.

Also described herein are suture passers that provide a tactile and/or audible feedback to the user when the tissue penetrator element is extended (e.g., fully extended).

Also described herein are suture passers that have extremely low profiles. In some variations the devices are adapted so that the lower jaw has a substantially lower profile by reducing the arc of the needle exit, by axially separating the lower jaw into a first (e.g., proximal) region controlling the axial translation (motion) of the lower jaw and a second (e.g., distal) region that contains all of the features of the tissue penetrator pathway; these different regions may have different heights, allowing nesting into the shaft particularly near the proximal end of the device.

Finally, described herein are suture cartridges and devices configured to be used with pre-loaded suture cartridges.

Although this disclosure is divided up into parts, indication different features, any of these parts or individual features may be used alone or in combination with any other parts or features described herein or incorporated by reference.

In general, the first or second jaw may hold the tissue penetrator within an internal passage, and the tissue penetrator may be extended between the distal-facing opening to push and/or pull a suture between the first and second jaws. The tissue penetrator may be any appropriate material, but shape memory materials (e.g., shape memory alloys, plastics, etc.) are of particularly interest. The tissue penetrator may have a sharp (e.g., pointed, beveled, etc.) distal tip for penetrating tissue. The tissue penetrator may be biased (e.g., pre-bent) in a curve or bend. In general the tissue penetrator (e.g., needle) may extend from a side region of the first or second jaw, extend across the distal-facing opening, and connect to an opening on the side region of the opposite (e.g., second or first) jaw from which it extends. This opening may include a suture capture region that holds the suture passed by the tissue penetrator. The suture capture region may be a suture retainer that holds the suture when passed by the tissue penetrator. For example, the suture retainer may be a deflecting or deflectable clamping region, a hook, or the like.

In general, the tissue penetrator may be configured to bend as it extends from the jaw and across the distal-facing opening. For example, the tissue penetrator may be pre-biased to assume a bent or curved configuration as it extends from within a jaw. Thus, the tissue penetrator may extend approximately perpendicular to the side of the jaw housing it. In some variations the jaw includes a tissue penetrator deflection (e.g., ramped) region that helps deflect the jaw. In some variations the jaw housing the tissue penetrator does not include a deflector.

For example, described herein are suture passers for forming a loop of suture around a target tissue, the suture passer comprising: an elongate body extending distally and proximally along a long axis; a first jaw extending from a distal end region of the elongate body wherein the first jaw is bent or bendable at an angle relative to the long axis; a second jaw configured to slide axially along the long axis distally and proximally relative to the elongate body, further wherein the first jaw and the second jaw form a distal-facing opening when the second jaw is extended distally and wherein the second jaw is retractable proximally so that it does not form the distal-facing opening with the first jaw; a tissue penetrator configured to extend across the distal-facing opening between the first jaw and the second jaw to pass a suture there between; and a plate having a keyhole capture region, wherein the keyhole capture region comprise a capture pathway including a channel extending through the plate and a release pathway, wherein the capture pathway is connected to the release pathway by at least one bend, further wherein the plate is coupled to the first jaw so that it may receive a suture from the tissue penetrator extending from the second jaw. The capture pathway may comprise an opening mouth at an edge of the plate that tapers to a narrower channel before the release pathway. In some variations, the release pathway comprises an enlarged opening having a larger diameter than the region of the capture pathway adjacent to the release pathway. The bend may be configured to retain the suture immediately after it is passed into the keyhole capture region by the tissue penetrator.

In some variations, the plate is configured as a suture stripper.

The device may also include a suture having an enlarged distal end region configured to be retained by the keyhole capture region, further wherein the diameter of the enlarged distal end region is greater than the diameter of the capture pathway but less than the diameter of a portion of the release pathway. The enlarged distal end region may comprise a knot.

Also described herein are methods of passing a loop of suture around a target tissue, the method comprising: placing a first jaw of a suture passer adjacent to a first side of a target tissue, wherein the first jaw extends from a distal end of an elongate body of the suture passer; extending a second jaw of a suture passer adjacent to a second side of the target tissue to form a distal-facing mouth with the first jaw, wherein the second jaw extends in a distal direction from the distal end of the elongate body of the suture passer; extending a tissue penetrator between the first and second jaws of the distal facing mouth while pushing a capture member connected to a suture with the tissue penetrator; retracting the tissue penetrator without the capture member or suture back between the first and second jaws of the distal facing mouth; repositioning the first and second jaws relative to the target tissue; extending the tissue penetrator between the first and second jaws of the distal facing mouth and capturing the capture member with the tissue penetrator; and retracing the tissue penetrator with the capture member back between the first and second jaws of the distal facing mouth.

The step of placing the first jaw may comprise placing the first jaw adjacent to the target tissue with the second jaw retracted proximally so that the distal end of the second jaw is adjacent or proximal to the distal end of the elongate body of the suture passer.

In some variations, the step of placing the first jaw comprises bending the first jaw relative to the elongate body.

Extending the tissue penetrator between the first and second jaws of the distal facing mouth while pushing a capture member may include extending the tissue penetrator from the second jaw to the first jaw. Extending a tissue penetrator between the first and second jaws of the distal facing mouth while pushing a capture member may comprise pushing a capture member comprising a flexible loop wherein the suture is connected to the flexible loop, or a plurality of flexible loops. Extending a tissue penetrator between the first and second jaws of the distal facing mouth while pushing a capture member connected to a suture with the tissue penetrator may comprise extending the capture member from a distal end of the first jaw member.

Also described herein are suture passer devices for passing a suture, the device comprising: an elongate body extending distally and proximally along a long axis; a first jaw extending from a distal end region of the elongate body wherein the first jaw is bendable at an angle relative to the long axis; a second jaw having a sharp, tissue penetrating distal tip, wherein the second jaw is configured to be manually slid axially along the long axis distally and proximally relative to the elongate body, further wherein the first jaw and the second jaw form a distal-facing opening when the second jaw is extended distally and wherein the second jaw is retractable proximally so that it does not form the distal-facing opening with the first jaw; a tissue penetrator configured to extend across the distal-facing opening between the first jaw and the second jaw to pass a suture there between; and a cam surface coupled to the second jaw and configured to move the second jaw axially in conjugate motion with bending of the first jaw member. The cam surface may be coupled with a trigger control configured to change the bend angle of the first jaw relative to the long axis. In some variations, the device further includes a control to engage or disengage the camp surface and engage or disengage the conjugate motion.

Also described herein are suture passer device for passing a suture and providing feedback to the user, the device comprising: an elongate body extending distally and proximally along a long axis; a first jaw extending from a distal end region of the elongate body wherein the first jaw is bent or bendable at an angle relative to the long axis; a second jaw having a sharp, tissue penetrating distal tip, wherein the second jaw is configured to slide axially along the long axis distally and proximally relative to the elongate body, further wherein the first jaw and the second jaw form a distal-facing opening when the second jaw is extended distally and wherein the second jaw is retractable proximally so that it does not form the distal-facing opening with the first jaw; a tissue penetrator configured to extend across the distal-facing opening between the first jaw and the second jaw to pass a suture there between; and an audible feedback actuator configured to provide an audible signal when the tissue penetrator is fully extended across the distal-facing opening.

BRIEF DESCRIPTION OF THE DRAWINGS

FIGS. 4A-4E illustrate various tear patterns that may be repaired using the invention described herein.

FIGS. 5A-5C show one variation of a suture passer.

FIGS. 6A, 6B, and 6D show top and two side perspective views, respectively of the distal end of the suture passer shown in FIG. 5A.

FIG. 6C illustrates the arrangement of the tissue penetrator and suture stripper in the distal end region of the suture passer of FIG. 5A.

FIGS. 9A-9C show variations of jaws (e.g., second jaws) of a suture passer. The variation shown in FIG. 9A includes a deflection region for deflecting a tissue penetrator at the widest point of the jaw profile. FIG. 9D shows the variation of FIG. 9A with the tissue penetrator extended. FIG. 9E shows the variation of FIG. 9B with the tissue penetrator extended. FIG. 9F shows the variation of FIG. 9C with the tissue penetrator extended.

FIGS. 12A-12I illustrate a variation of a suture passer describe herein, adapted to pass a suture through the tissue twice without having to re-load.

FIGS. 16A-16G illustrates a suture passer device and suture capture element passing a suture twice through a target tissue to form a loop of suture around the target tissue.

FIGS. 18A-18I show operation and aspects of a suture passer using an expandable capture element.

FIGS. 24A-24C illustrate a suture passer device having an audible/tactile feedback indicating the extension of the tissue penetrator.

FIG. 25A shows a section through a "thin" variation of a suture passer. FIGS. 25B-25D illustrate enlarged views of various region of the suture passer of 25A.

FIG. 26 shows the distal end region of the suture passer of FIG. 25A.

FIGS. 27A and 27B show portions of the suture passer of FIG. 25A adapted to reduce the height of the device.

DETAILED DESCRIPTION

Described herein are sutures passers. These suture passers may be used arthroscopically, and may be used to pass one or more length of suture. In general, the suture passers described herein include an elongate body and a first jaw member (e.g., first jaw) extending from the distal end of the elongate body, wherein the first jaw is bent or bendable relative to the distal to proximal axis of the elongate body. In some variations the first jaw is hinged near the distal end region of the elongate body. Some variations of the suture passers described herein include a second jaw member (e.g., second jaw) that is configured to slide axially (proximally and distally) relative to the elongate body and/or first jaw. The second jaw may be configured to slide axially sufficiently far proximally so that the distal tip of the second jaw is proximal to the distal end of the shaft (e.g., completely retracted). The first and second jaws may be configured to form a distal-facing opening into which tissue may be held. The suture passers described herein may also include a flexible, bendable, or pre-bent tissue penetrator for passing a suture through the tissue. The suture passer may also include a handle at the proximal end with one or more controls for actuating the first and/or second jaws and the tissue penetrator.

In some variations, described herein are suture passer having very narrow second jaws; the tissue penetrator may exit the second jaw from the side of the second jaw and extend across a distal-facing opening to engage an opening in the opposite jaw (e.g., the first jaw), where a suture may be secured and/or released. For example, the suture passers described herein may have a second jaw having a maximum diameter (e.g., maximum height) along the length of the second jaw of less than about 0.11 inches, 0.10 inches, 0.09 inches, 0.08 inches, 0.07 inches, 0.06 inches, 0.05 inches, 0.04 inches, 0.03 inches, 0.2 inches, 0.01 inches, etc. The second jaw may be any appropriate width. For example, the width may be approximately 0.15 inches.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all subranges subsumed therein.

Figure 1B:
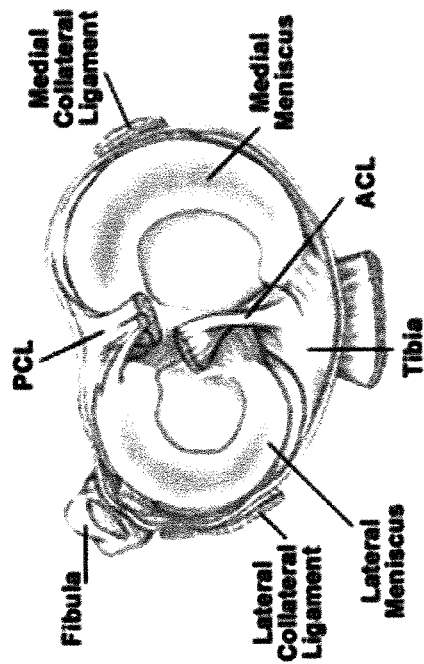
FIGS. 1A and 1B illustrate the anatomy of the meniscus, one exemplary tissue that may be sutured using the devices described herein.
Figure 1A:
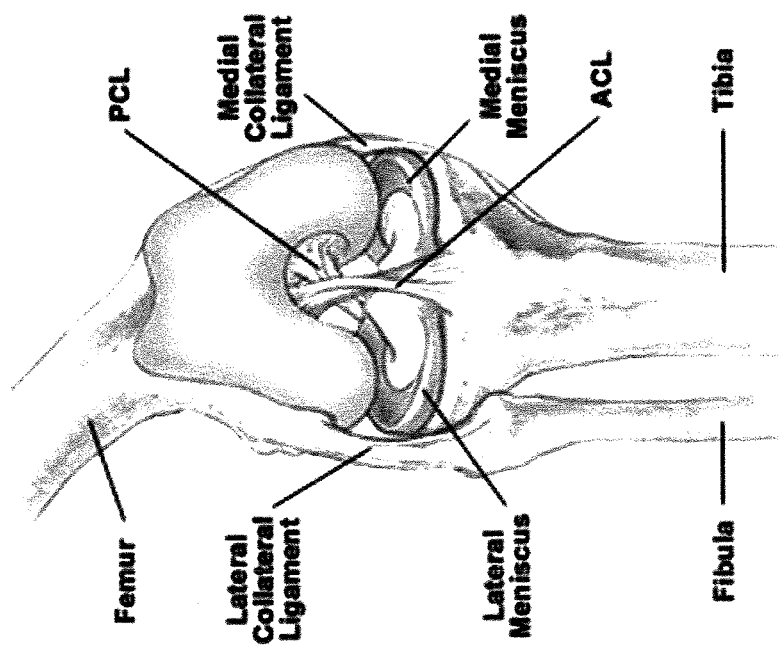
Figure 2:
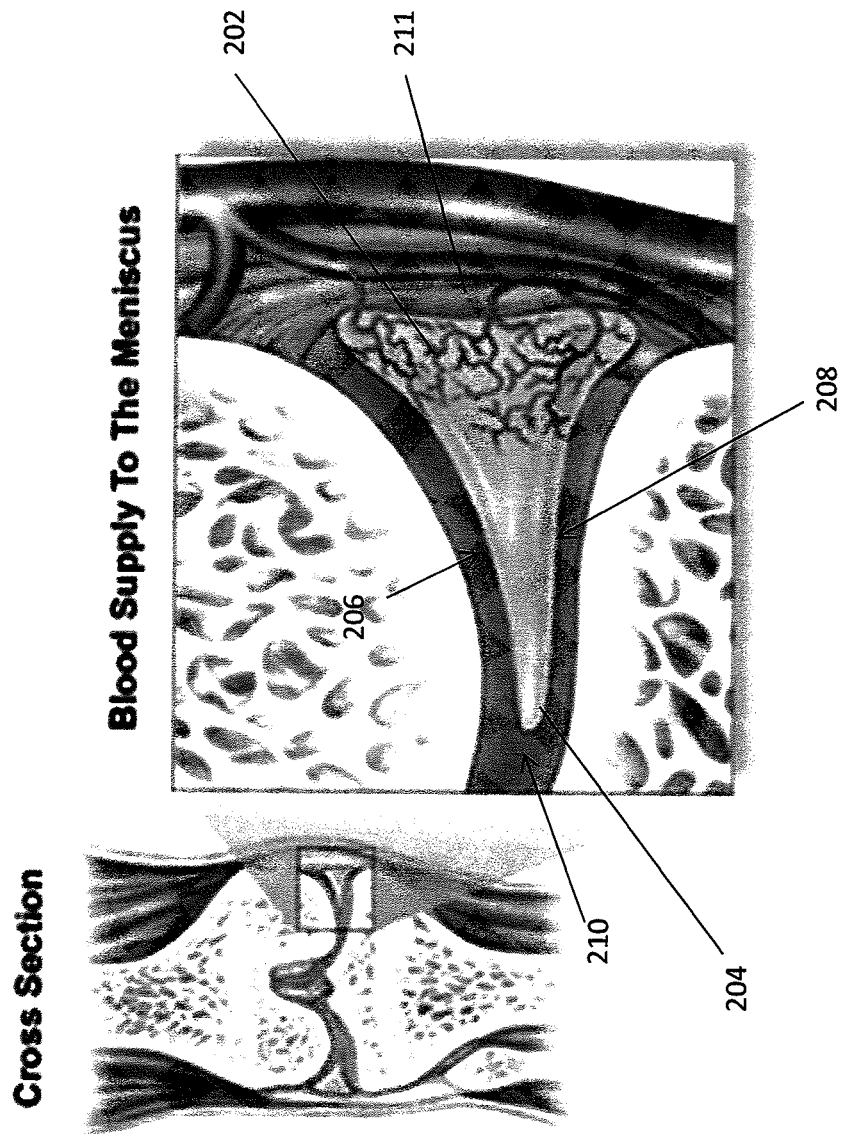
FIG. 2 illustrates the anatomy of the meniscus, including the capsule and associated vascular tissue.
Figure 3:
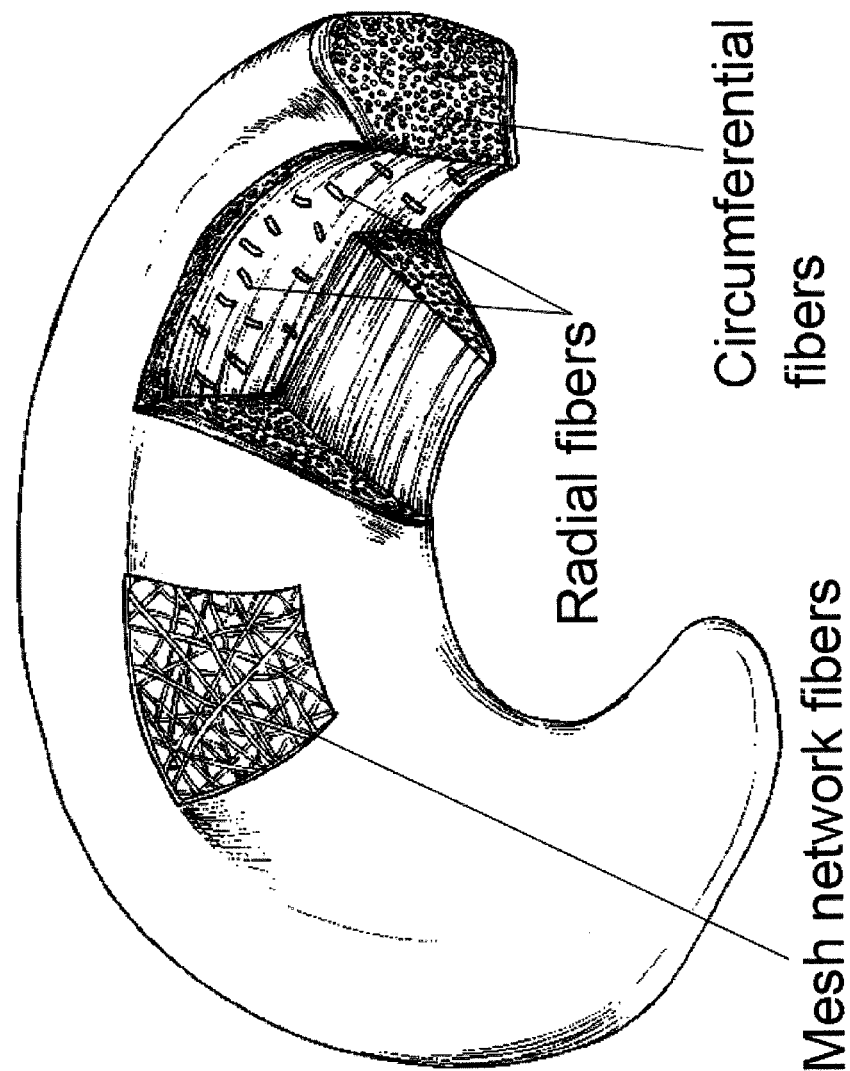
FIG. 3 illustrates the structure of a meniscus.
Figure 5C:
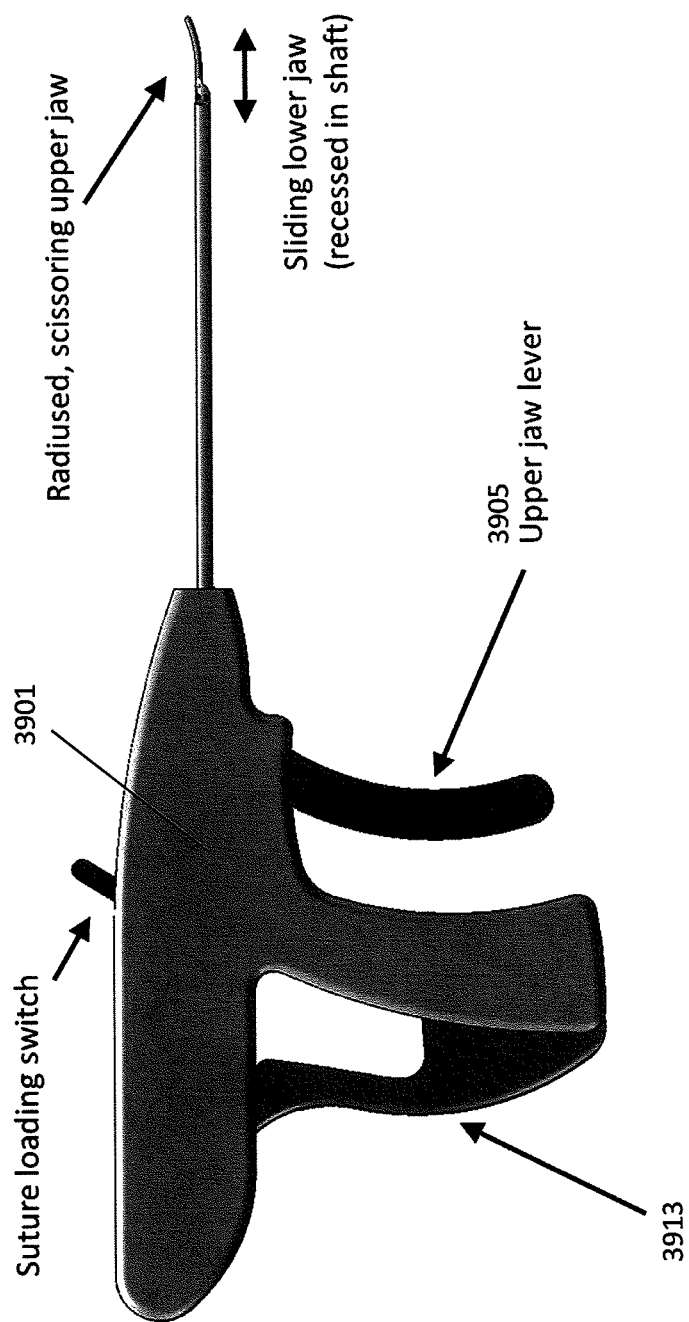

FIGS. 5A-5C illustrate suture passers that have a first jaw and a second jaw that may be controlled to form a distal-facing opening across which a tissue penetrator may extend to pass a suture through tissue between the first and second jaws. For example, in FIG. 5A, the suture passer of has a tissue penetrator that extends distally from a distal opening in the first jaw. In this example, the tissue penetrator travels in a sigmoidal path (e.g., approximately "S-shaped", and is deflected twice, once upon leaving the lower jaw, and once upon contact with the upper jaw) from out of the second jaw, though any intervening tissue, to first jaw. One or more length of a suture (including two lengths of the same suture, e.g., two ends of the same suture) can be loaded (including pre-loaded) into the device and passed through the tissue. The suture passer show in FIGS. 5A-5C is also configured so that the first (e.g., upper) jaw can pivot to assume a different angle relative to the elongate body of the device, and the second jaw is axially slideable or extendable distally from the distal end of the elongate member to form a distal-facing mouth with the first jaw. The proximal handle includes a plurality of controls for controlling the pivoting of the first jaw, the axial sliding of the second jaw, and the extension/retraction of the tissue penetrator from the second jaw.

FIG. 5B shows the device of FIG. 5A with the outer housing of the proximal handle 3901 removed, revealing some of the connections between the controls and the device. In FIG. 5B, the distal most control 3905, the proximal handle is configured as a trigger or lever that controls the motion of the first jaw ("first jaw control"). The first jaw control may be pulled to reduce the angle of the first jaw relative to the long axis of the elongate member 3907. In this variation the first jaw control is pinned and allowed to drive a tendon in the elongate member distally when compressed to drive the first jaw down (reducing the angle between the first jaw and the long axis of the elongate member). This pivoting motion may also be referred to as scissoring (scissoring motion).

A distal control 3913 is also configured as a lever or trigger, and may be squeezed or otherwise actuated to extend and/or retract the second jaw to form a distal-facing mouth with the first jaw, as shown in FIGS. 5A-5B. In some variations the control is further configured to control deployment of the tissue penetrator in the sigmoidal path. For example, in some variations squeezing the distal control after completely extending the second jaw may deploy the tissue penetrator from the second to the first jaw so that the distal end of the tissue penetrator extends out of the first jaw. As it extends between the first and second jaw, the tissue penetrator may carry a first length (bight) of suture through the tissue. Upon reaching the opposite jaw, the suture may be removed from the tissue penetrator and held (e.g., by a stripper) in the first jaw. Upon release of the distal control, the tissue penetrator may withdraw back into the second jaw. Actuating (e.g., squeezing) the distal control 3913 again may result in the extending the tissue penetrator (along with any second length of suture) back through the tissue from the second jaw to the first jaw, where the second length of suture can be retained. Alternately, in some variations, the controls (e.g., to control motion of the first and/or second jaw) may be separate from each other, and/or from extending/withdrawing the tissue penetrator. Additional controls may also be included in the proximal handle, include a suture loading control (e.g., switch, toggle, etc.) for loading and/or tensioning the suture within the second jaw.

FIGS. 6A-6D show an enlarged view of the distal end of the device of FIGS. 5A-5C. For example, in FIGS. 6A and 6B the first jaw 4003 is thin and slightly radiused (e.g., curved), and is hinged to the elongate shaft region of the device. The first jaw is also connected to a control (handle, etc.) on the proximal handle by a push/pull member (tendon, wire, rod, etc.), allowing adjustment of the angle of the first jaw relative to the elongate member.

Figure 6D:
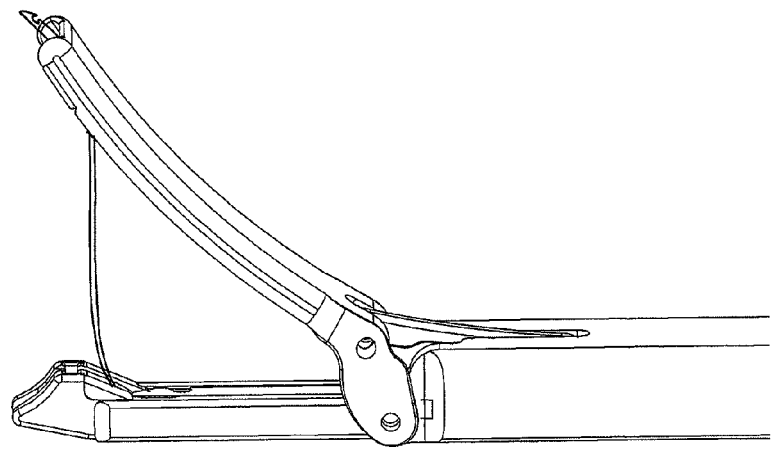
Figure 8B:
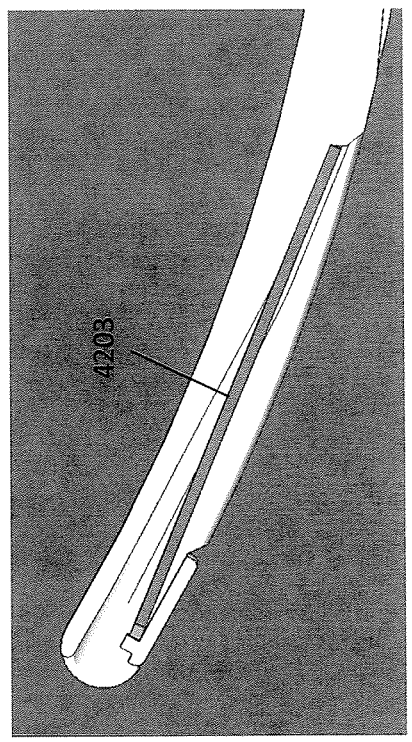
FIGS. 8A and 8B show side perspective views of the distal end region of a jaw including a suture stripper.
Figure 8A:
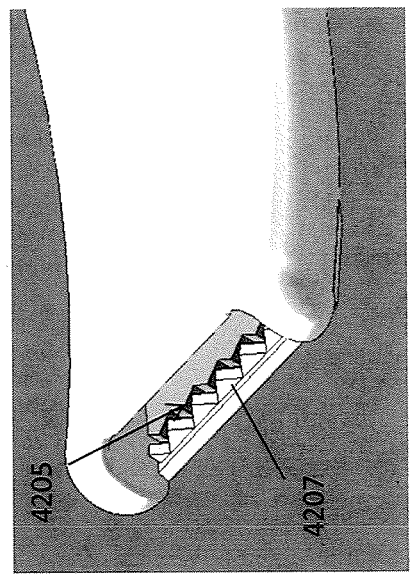

In FIG. 6C, the first and second jaws have been removed from the distal end of the device shown in FIG. 6B, revealing the tissue penetrator 4007 within the second jaw and a suture stripper 4009 (suture retainer) in the first jaw. FIG. 6D shows the distal end of the device of FIG. 6B after the tissue penetrator has been extended across the distal-facing mouth. FIGS. 8A and 8B illustrate one variation of a first jaw region having a suture stripper. In FIG. 8A, the suture stripper is visible from the distal opening at the distal end of the jaw. In this example, the stripper includes a stripper plate 4203 with a saw-toothed edge 4205. The jaw also includes a receiver region for the stripper plate having a sawtooth edge 4207.

Figure 7A:
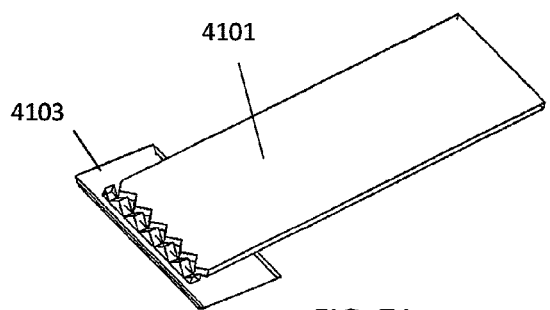
FIGS. 7A-7C show a suture stripper including a stripper plate (FIG. 7B) and base (FIG. 7C).
Figure 7C:
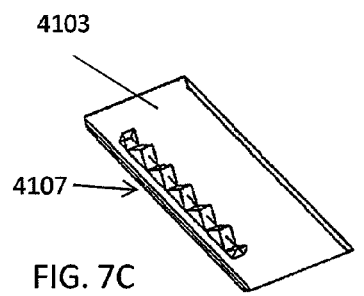
Figure 7B:
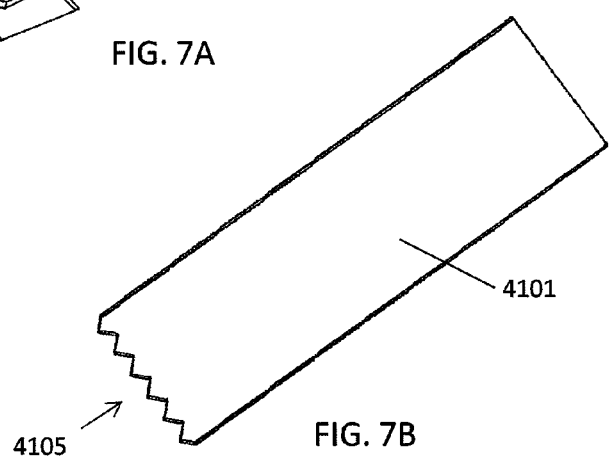

FIGS. 7A-7C show greater detail on one variation of a suture stripper that may be used. This variation is the same as the variation shown in FIGS. 8A and 8B. Although the examples provided herein show the suture stripper in the first jaw, in some variations a suture stripper may be present on the second jaw (e.g., where the tissue penetrator is configured to pass a length of suture from the first jaw to the second jaw). In FIG. 7A, the stripper includes a flexible plate 4101 that is fixed at the proximal end (e.g. to the first jaw), and pressed against a receiving plate 4103 at the distal end 4105. In some variations the receiver is not a separate receiving plate, but merely a region of the jaw. Either or both the suture stripper plate 4101 and the receiver 4103 may include an edge that is adapted to catch the suture. In FIGS. 7A-7C, both the plate 4101 and receiver 4103 include edges having teeth 4105 and 4107. In this example the teeth are saw-tooth structures that are adjacent (or abutting) in the first jaw. The tissue penetrator may pass between the plate 4101 and the receiver 4103 by deflecting the plate 4101; as the end of the tissue penetrator passes the edges 4105 and 4107, a length of suture held by the tissue penetrator may be caught by the stripper and held between the plate and receiver as the tissue penetrator is withdrawn. In practice, a suture passer having a distally-extending tissue penetrator (including a pre-tied knot) may be used to repair a tissue such as the meniscus of the knee.

The devices and methods described herein may be used to pass a loop of suture and specifically, may be used to form a vertical or horizontal stitch to repair tissue. When repairing the meniscus, a vertical stitch typically provides the strongest repair with the least amount of displacement relative to horizontal stitches or other "all-inside" approaches. The devices and methods described herein may also be referred to as "all-inside" devices and meniscal repair techniques allow the meniscus to be sutured directly. The suture passers described herein may place a fully-circumferential, vertical stitch around meniscal tears. This stitch may provide uniform compression along the entire height of the meniscus and maintain coaptation of the tear at both the inferior and superior meniscal surfaces. Further, because of the jaw and needle configuration, the distal extending tissue penetrator does not penetrate the capsule wall, reducing or eliminating risk to posterior neurovascular structures. These features may allow a greater healing response due to complete tissue coaptation along the entire substance of the tear, improved clinical outcomes due to the greater healing response and to the anatomic reduction and fixation of the meniscus tear, may avoid scalloping or puckering of the meniscus, and may result in less extrusion or peripheralization of the meniscus caused by over-tensioning of suture or hybrid tensioners to the capsule. These devices can also be used to treat radial, horizontal, flap, and other complex tears in addition to longitudinal tears.

In some variations, the suture passer devices described herein can be fired blindly where arthroscopy camera access is poor, as knee structures are protected from the needle path.

Returning now to FIGS. 5A-5C, as mentioned above, the device (e.g., in FIG. 5C) has a scissoring first jaw that is curved (radiused). This curve may be configured to follow the radius of the femoral condyle. The second jaw in this example is relatively straight. The second jaw may be recessed (partially or completely) into the shaft, and may slide proximal-to-distal in order to slide under the meniscus along the tibial plateau after the first jaw is in place along the superior surface of the meniscus. The second jaw in this example contains a flexible needle, which moves vertically from the second to first jaw.

In some variations a knot of suture may be passed through tissue using a suture passer as describe above in which a pre-tide knot is used to help secure the length of suture being passed to the device. For example, in some variations an end region of one or both (in variations in which two lengths of suture are being passed) lengths of suture are knotted, and this pre-tied knot may be passed through the tissue by the tissue penetrator. The pre-tied knot may or may not include a leader snare. For example, in some variations two lengths of suture (from the same elongate suture) may be passed through a tissue; both lengths may be pre-knotted, however only one of the pre-tied knots may include a leader snare and be configured to allow another length of suture to be pulled through using the leader snare.

In some variations, the suture passers described herein may include a second (e.g., lower) jaw that is thin (e.g., <0.11 inches in diameter at the widest point). In general, thinner second jaws may be inserted into narrower and difficult to access body regions. In some variations, in which the second jaw houses the tissue penetrator and the tissue penetrator extends across the distal-facing opening formed between the first and second jaw, the second jaw may include a deflection ramp or deflection structure to help deflect the tissue penetrator out of the jaw and across the distal-facing opening. The deflection ram or deflection structure in some variations may form a widened region of the second jaw. Although it was initially believed that this enlarged deflection region was necessary to provide sufficient deflection and control of the motion of the tissue penetration, recent information suggest that this may not be necessary, particularly when using a pre-bent or pre-biased shape memory material to form the tissue penetrator. Thus, as shown in FIGS. 9A to 9C, second jaws housing a tissue penetrator may be used, wherein each one has a different thickness and/or different size deflection region. For example, in FIG. 9A the second jaw includes a deflection region 907 distal to the opening from which the tissue penetrator may be extended (extension of a tissue penetrator is illustrated in FIG. 9D). The widest diameter portion 901 of the jaw in this example is the deflection region 907. In some variations the widest diameter region is less than approximately 0.15 inches (e.g., less than about 0.14 inches, less than about 0.13 inches, less than about 0.12 inches, less than about 0.11 inches, less than about 0.10 inches).

Although a protruding deflection region may be helpful for steering the tissue penetrator/needle as it leaves the jaw, surprisingly, in some variations a protruding deflection member is not necessary, allowing the diameter of the jaw to be thinner. For example, in FIG. 9B, a jaw housing a tissue penetrator is shown without a protruding deflection member. FIG. 9E shows the jaw of FIG. 9B with a tissue penetrator 905 extending from the side of the jaw. In this example, the jaw is thinner than the example shown in FIG. 9A; the maximum diameter (e.g., maximum height) of the jaw 911 is less than about 0.10 inches (e.g., less than 0.09 inches, less than 0.08 inches, less than 0.07 inches, less than 0.06 inches, etc.). FIG. 9C shows another example in which the jaw is even thinner (e.g., less than 0.06 inches, less than 0.05 inches, less than 0.04 inches, less than 0.03 inches, etc.). In any of these examples the jaw may have a width. For example in some variations the width is between about 0.01 inches and about 0.15 inches. The tissue penetrator is typically thinner and narrower than the jaw so that it may fit within the jaw; the tissue penetrator (e.g., needle) may have a square, round, rectangular, or other cross-sectional area. In general, the tissue penetrator may be configured as a ribbon-shaped tissue penetrator, having a sharp (e.g., pointed, beveled, etc.) distal tip region, and a suture retaining region (e.g., hook, eyelet, etc.).

Any of the jaws illustrated in FIGS. 9A-9F may be used as a second or lower jaw for a suture passer as illustrated above (e.g., FIGS. 5A-6B). In general, the suture passers shown in FIGS. 5A-6B include first and second jaws having atraumatic (e.g., non-tissue penetrating) distal tip regions. Thus, as illustrated in these figures, the distal tip region of both jaws (first and second) are rounded and atruamatic so that they do not readily penetrate or cut the tissue. However, in some variations, the distal tip region of a jaw is tissue penetrating, allowing the jaw to be inserted into the tissue. In particular, it may be beneficial to have the axially slideable jaw (e.g., the second jaw) be tissue penetrating so that it can be extended into the tissue. This may allow the suture passer to pass a suture in an angle within the tissue (including at a right angle, e.g., to form an approximately "L" shape).

A mentioned above, it may be beneficial to minimize the height of the distal end, and particularly the lower jaw and/or upper jaw at the distal end of the device. It may also be beneficial to reduce the height of the elongate body of the device. Described herein are designs configured to provide minimal height to the elongate body and/or lower and/or upper jaw.

For example, in some soft tissue repair situations, getting access into tight spaces is necessary for accessing the soft tissue requiring repair and for preserving the tissues adjacent to the repair site. An example is a torn meniscus where the knee ligaments can limit the space between the femur and tibia to as little as 3.5 mm. The femur and tibia are covered in cartilage which must be preserved in order to maintain proper joint health. Therefore a suture passer that has a shaft height of 3.5 mm or less provides significant clinical utility to the surgeon. In a suture passer embodiment that contains a sliding lower jaw, as described above, the minimum height is dictated by minimizing specific dimensions. For example, FIG. 25A shows a cross-section through a variation of a suture passer having a sliding lower jaw. Exemplary dimensions that contribute to the overall device height include: the height of the lower jaw 2505 in order to contain the needle pathway, the height of the needle shaft 2511, the height of the clamp rod 2509, the height of the shaft 2507 necessary to maintain appropriate strength, and the height of the clamp link 2513. These heights are illustrated in the enlarged views of the lower jaw (FIG. 25B), elongate body (FIG. 25C), and clamp link 2506 region (FIG. 25D). Even a small reduction in any of these heights, without sacrificing the performance parameters, may provide substantial gains in how and where the suture passer may be used.

For example, in one variation, a number of architectural changes may be made that facilitate a shorter overall height of the instrument. First, the lower jaw pathway may be truncated so that the arc in the lower jaw does not turn fully to 90 degrees, as previously described. See, e.g., FIG. 25B. If, instead, the needle may be configured to exit the lower jaw at a shallower angle (<90°, such as approximately 80°, approximately 70°, approximately 60°, etc.) while still contacting the upper jaw in a region sufficient for deflection distally to pass the suture as described above.

In some variations, a structural portion of the shaft that connects the two sides of the shaft together has been moved from the top to the bottom. This change is facilitated by breaking the lower jaw into two pieces, a first (e.g., distal) end part that contains all of the features of the needle pathway, and second (e.g., proximal) part that serves to translate the position of said distal end. The second, more proximal, piece is not as tall as the distal piece so that it can nest within the shaft. The jog in height is shown in FIG. 26. In this example, the distal end 2607 of the lower jaw contains the needle pathway, while the proximal end 2605 include the strucutre spine of the shaft. The transition between the two 2609 allows for a very flat profile.

In some variations, the height of the needle shaft and clamp rod are reduced. The clamp rod may move to actuate the hinged upper jaw. For example, the clamp rod 2701 may be made flat and attached to the shaft 2709 using a tongue-in-groove configuration while communicating through the open top in the shaft 2709, as illustrated in FIG. 27A. The needle shaft 2703 passes below the clamp rod over this portion of the elongate body. The lower jaw translation shaft 2705 is a U-shaped element within the shaft 2709 that partially surrounds the needle shaft 2703. The combination of these features minimize the amount of material needed to keep the necessary strength and rigidity.

Figure 27B:
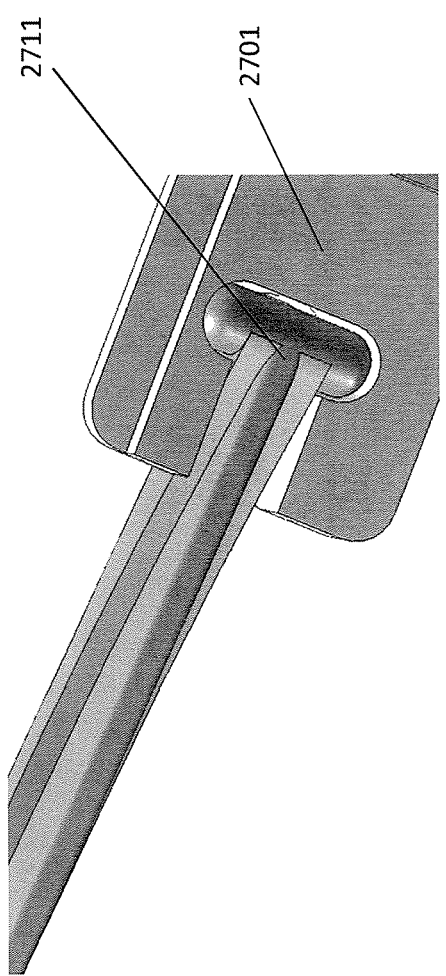
Figure 28A:
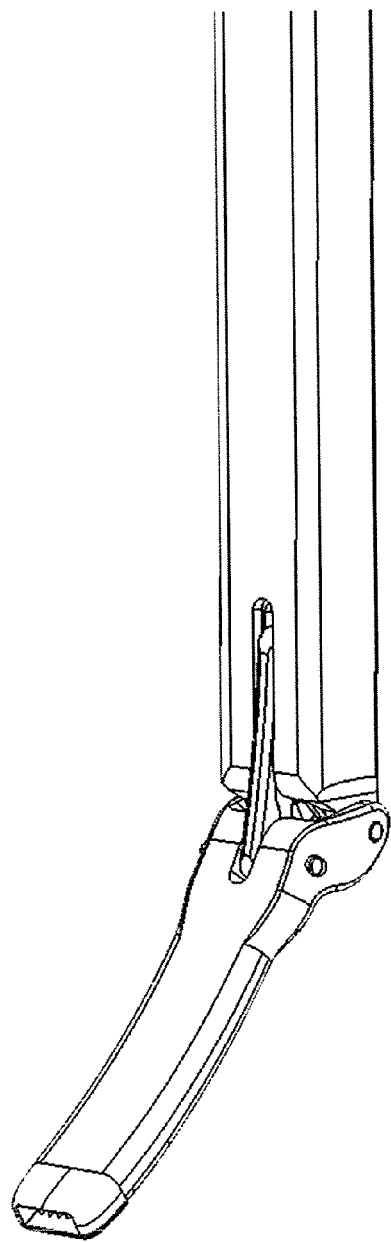
FIGS. 28A and 28B show examples of suture passers having full elongate body housing (FIG. 28A) and a partial or c-shaped elongate body housing (FIG. 28B) from a top perspective view.
Figure 28B:
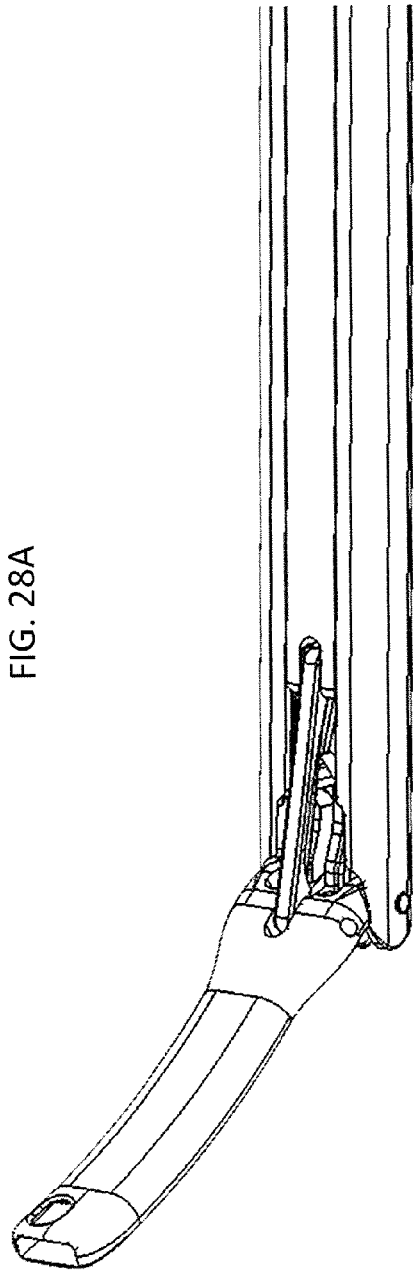
Figure 29A:
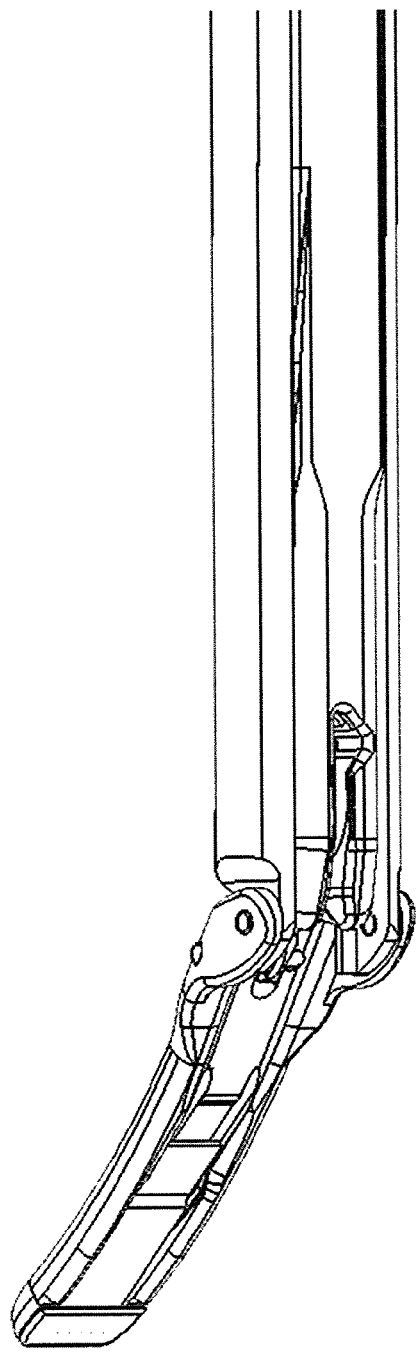
FIGS. 29A and 29B show bottom perspective views of the same suture passers of FIGS. 28A and 28B, respectively.
Figure 29B:
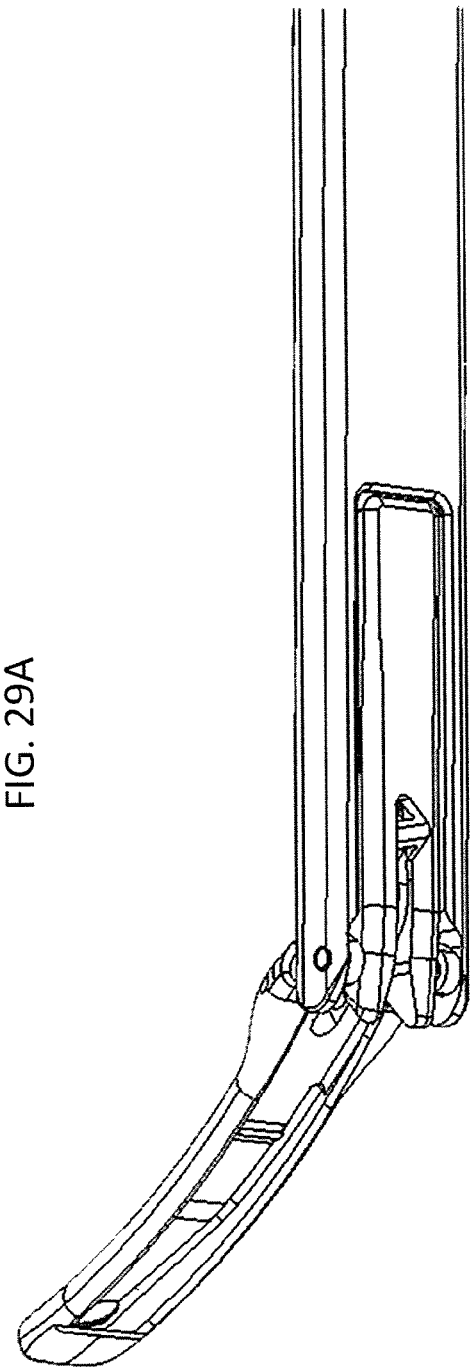

In some variations, the clamp link (which contributes to the hinged motion of the upper jaw) is changed from having two holes with pins through them as shown in FIG. 6D to an alternate design that replaces the more proximal hole with a pin that is integrated into a the clamp link such that it mates with the clamp rod in a the manner shown in FIG. 27B.

Thus, any of these features may be combined to reduce the height of the suture passer devices having an elongate shaft, as shown. For example, the elongate body may have a U-shaped cross-section. The upper jaw actuator ("clamp rod") may be coupled to the hinge (clamp link) via a recessed connection within the footprint of the elongate shaft at one end, and within the upper jaw at the other end, as shown in FIG. 27A. Further the lower jaw member may include a distal region that controls the needle actuation and a proximal region that includes the linear actuating components.

FIGS. 28A-28B and 28A-29B compare a device that does not include the U-shaped outer housing and recessed hinge (FIGS. 28A, 29A) with a device that does (FIG. 28B, 29B) in top (FIGS. 28A-28B) and bottom (29A-29B) perspective views.

Passing a Loop of Suture Through Tissue

The suture passers described herein may be used to pass a suture in a loop though tissue, so that the ends of the suture can be approximated (e.g., tied together, anchored, etc.). In some variations the suture passer may be loaded with a first length of suture, the first length of suture passed through the tissue, then the suture passer can be reloaded with a second length of the suture and repositioned, and the second length of the suture can then be passed through the tissue again.

Figures 10A, 10B, 10C, 10D, 10E, 10F, 10G, 10H:
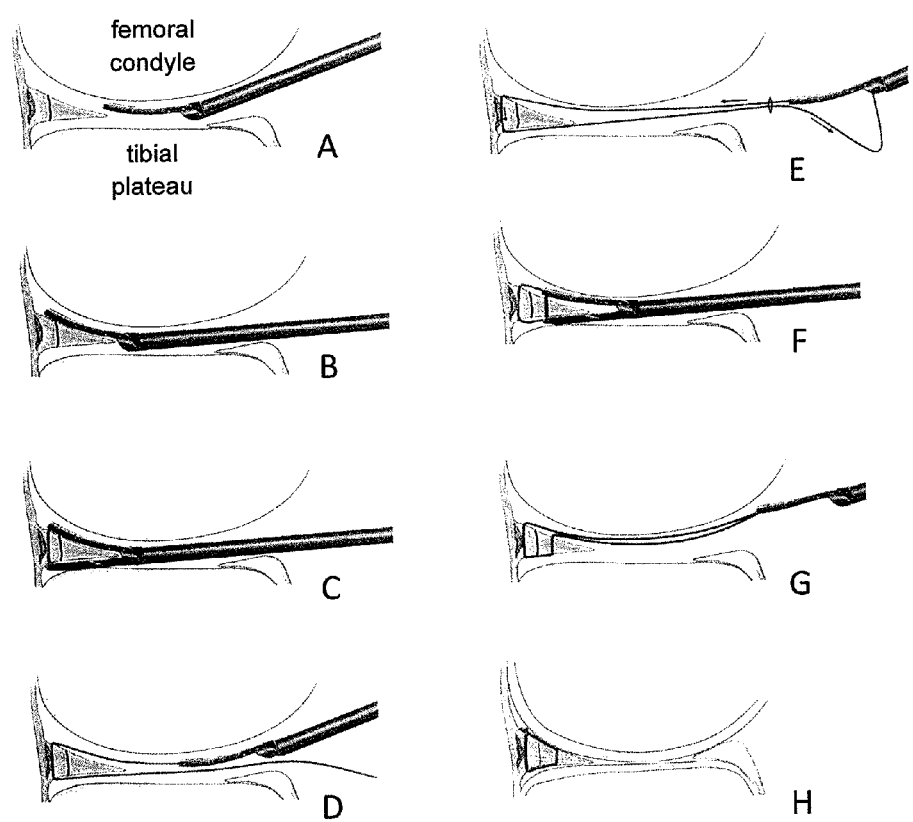
FIGS. 10A-10H illustrate use of a suture passer described herein to form a loop around a target tissue.

For example, FIGS. 10A-10K illustrate on method of forming a loop through tissue in a meniscus. As illustrated, a suture passer (similar to the suture passer shown in FIGS. 5A-6D) can be inserted through a working portal and advanced until the upper jaw is between the superior surface of the meniscus and the articular surface of the femoral condyle (FIGS. 10A-B). The lower jaw is then extended forward so that it moves under the meniscus and the tissue penetrator (needle) trigger is actuated to complete the peripheral pass of the suture from the lower jaw to the upper jaw where it is atraumatically self-retained (FIG. 10C). The lower jaw is retracted and device is removed (FIG. 10D). The suture passer is then re-loaded with the opposite suture strand and re-inserted while gently pulling on the suture such that the upper jaw is lead into the exact same tissue plane (FIG. 10E) the suture is again passed from lower jaw to upper jaw, this time positioned on the opposite side of the tear (FIG. 10F), and the lower jaw is again retracted and the device removed (FIG. 10G). A knot can then be tied on the peripheral femoro-synovial junction (shown in FIG. 10H). No cannula or sled are required for this technique, and the method avoids tissue bridging that can occur if the suture re-enters the tissue in a slightly different location.

In some variations, the suture passer may be adapted so that the device does not need to be withdrawn out of the tissue to be loaded with the second suture. For example, the first and second (or more) lengths of suture may be pre-loaded onto the suture passer. For example, the suture passer may be adapted so that the tissue penetrator (needle) is adapted for both pushing a suture from the lower jaw to the upper jaw and pulling suture from the upper jaw back to the lower jaw (or vice-versa).

The suture passer devices described herein may be configured so that the end of the suture, or a suture linked element connected to the suture, is first pushed by the tissue penetrator through the tissue from the first (e.g., lower, axially moving) jaw to the second (e.g., upper, bending) jaw, then the device is moved relative to the tissue and the tissue penetrator is then extended to collect the end of the suture or the suture linked element, and retracted back through the tissue to pull the suture back through the tissue. Thus, a full stitch may be passed through the tissue. In the meniscus, the full stitch may be passed within the joint capsule without removing the device between passes.

An exemplary sequence of operation is as follows: with a suture loaded onto the device, the device is inserted into the joint capsule and place the device in position for the first pass; pass ("fire") the first leg of the suture; move the device to the second location; fire the device to retrieve the suture, and remove the device from the joint capsule. The suture can then be released from the device and the knot tied (closing the suture loop). This method and devices for implementing it may be referred to as "push/pull" since one end of the suture is first "pushed" through tissue by the needle and captured in the upper jaw, and it is then moved to the second position, and the needle comes up through the tissue to retrieve the captured end and pulls it back down into the lower jaw.

Figure 11A:
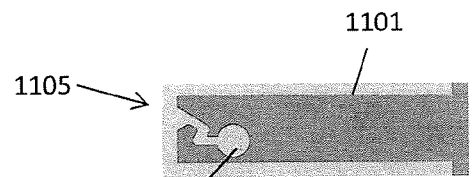
FIGS. 11A-11D illustrate one variation of a suture passer as described herein, adapted to pass a suture through the tissue twice without having to re-load.

In a first variation, a suture that is loaded into the suture passer containing a suture retaining plate on the second jaw that is configured to releasably hold the distal end of a suture, where the plate is adapted to have a "keyhole" passage 1101 through which the suture may be entered and temporarily retained. In some variations this retaining plate with the keyhole is a stripper plate as shown and described above, but with the addition of the keyhole structure. In some variations the keyhole retaining plate is positioned adjacent to a suture stripper. This keyhole suture retainer on the plate and/or suture stripper has an opening at one end that has a larger diameter than the suture; the passage connecting the edge of the suture (which may have a large mouth 1105 that narrows to the narrower passage) typically has a narrower diameter ($D_p$). The keyhole passage typically includes a bend or bends (elbow region) before opening into the large opening mentioned. The elbow region may retain the suture in this narrow region until the tissue penetrator extends back across to retrieve it, as will be described below. FIG. 11A illustrates one variation of a suture stripper 1101 with such a keyhole passage. This variation may be used with a suture having an enlarged distal end feature, such as a knot, ferrule, or other enlarged region attached to the distal end (or near the distal end) of the suture. One embodiment of this enlarged distal end feature of the suture is an overhand knot tied at the end of the suture. A second embodiment is a plastic or metal part that is overmolded, glued, tied or otherwise affixed to the end of the suture. In this embodiment, the stripper with the keyhole cutout may capture the enlarged region of the suture on the end of the suture. As described above, the adapted suture stripper is attached to the inferior surface of the upper jaw. See, e.g., FIGS. 11A-11Cc. The keyhole cutout region 1105 is shaped in a fashion that allows it to hold the suture at various states while facilitating release of the suture during the second phase (pull) of the procedure. The keyhole-adapted stripper 1101 may be made from any appropriate material, including plastic or sheet metal.

Figure 11B:
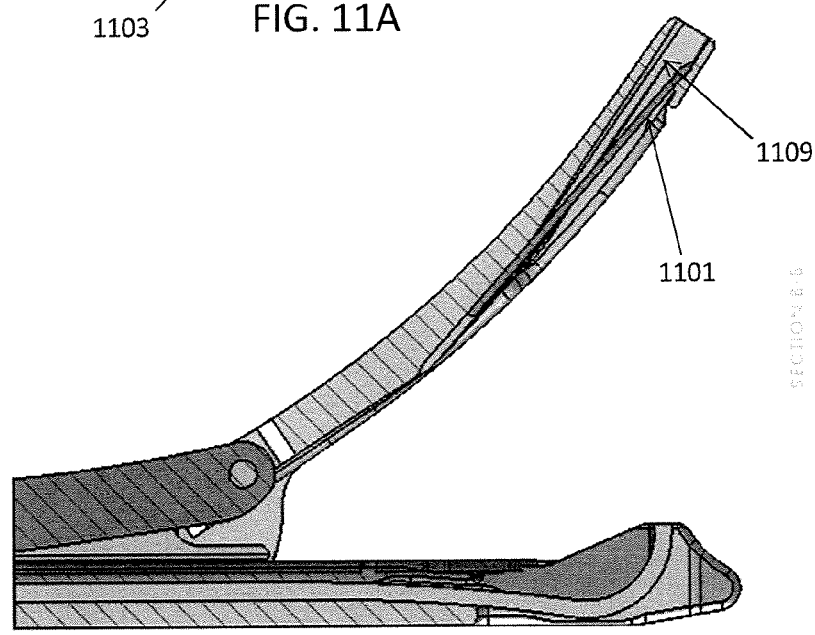
Figure 11C:
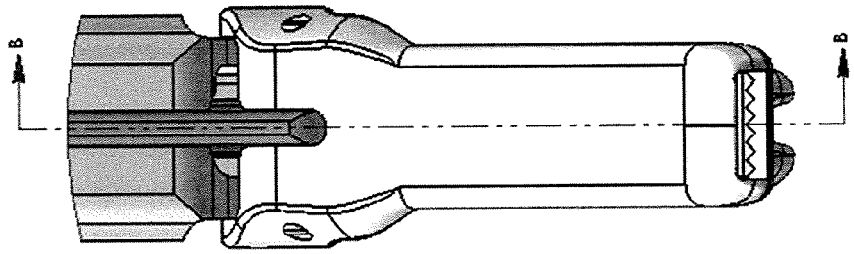
Figure 11D:
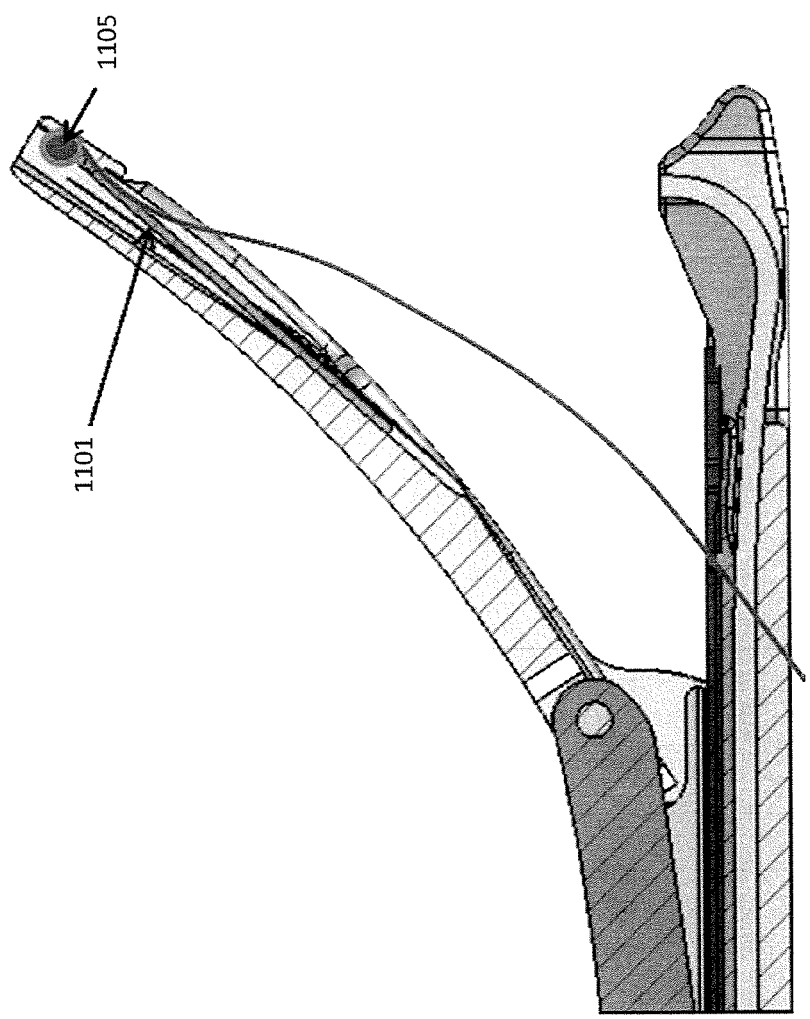

FIG. 11B shows the distal end of a suture with an upper jaw member that includes the plate having a keyhole opening. In this example, a separate suture stripper 1109 is positioned above the plate with the keyhole feature. A tissue penetrator may pass under the suture stripper and the plate with the keyhole feature and the stripper scrapes the suture off the tissue penetrator as the tissue penetrator retracts. FIG. 11C illustrates a top view of the upper jaw of FIG. 11B, showing the distal end of the jaw, with the opening 1105 into the keyhole region that narrows to guide the suture into the bend/elbow region and eventually to the larger opening. FIG. 11D shows the distal end of the suture passer after the suture with the enlarged distal end feature 1105 has been deposited into the keyhole cutout 1101 of the upper jaw.

Figure 12F:
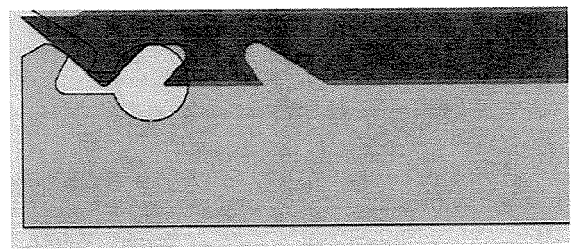
Figure 12E:
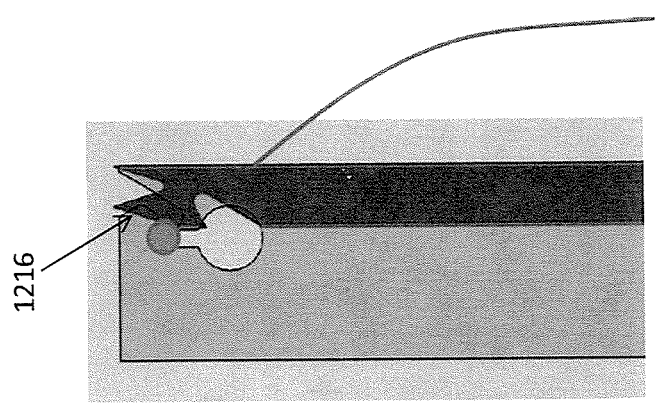
Figure 12D:
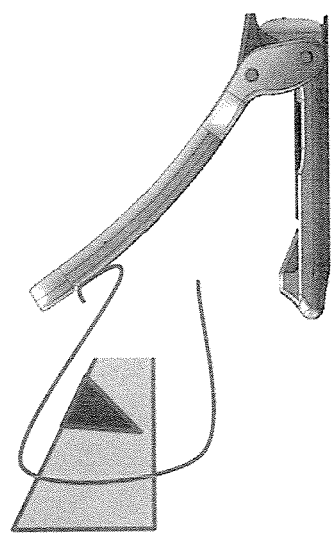
Figures 12G, 12H, 12I:
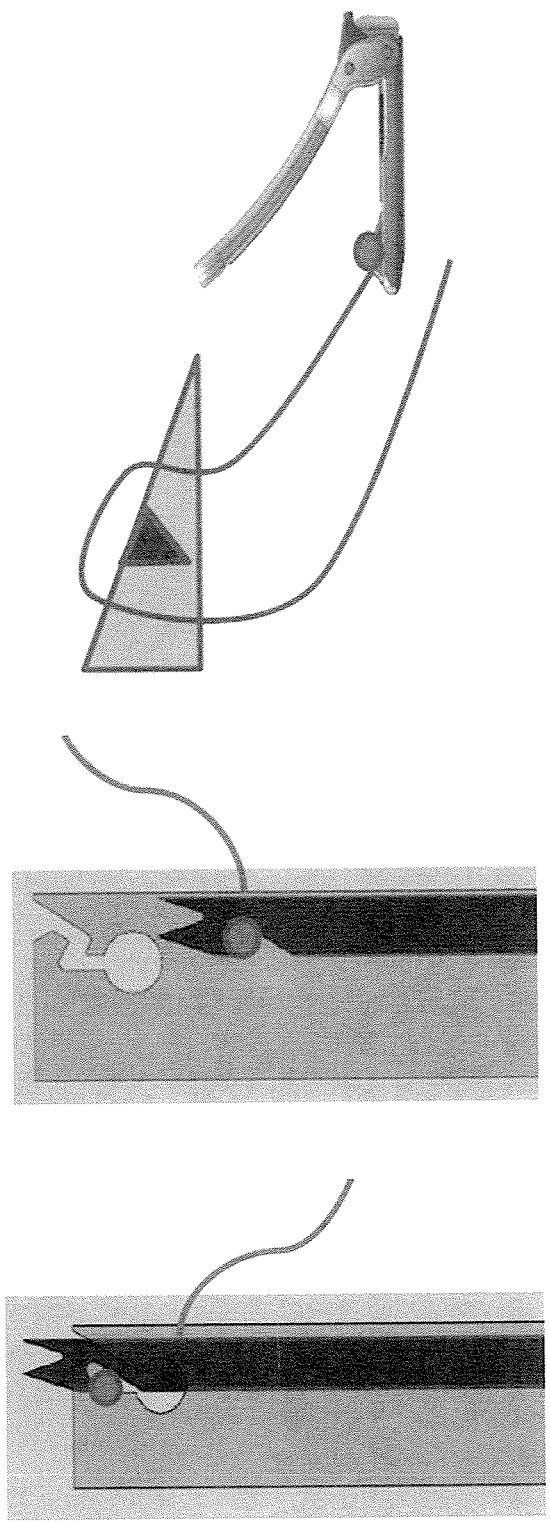

FIGS. 12A-12B illustrate operation of the plate with the keyhole cutout feature 1201 and a suture with an enlarged distal end feature 1205. In FIG. 12A, the needle is shown beneath the trap feature (the keyhole cutout 1201), which has been made transparent to show the needle position. The enlarged distal end feature 1205 enters the keyhole cutout through the large opening at the edge. The needle passes the first leg of the suture and the knot at the end of the suture (enlarge distal end feature 1205 of the suture). The needle then retracts, leaving the knot and suture behind, and tension is applied to the suture to locate it securely in the correct position, as shown in FIG. 12B. FIG. 12C shows a side perspective view of the method being applied in a meniscal tear (tissue 1211 with tear 1214). The suture passer may be placed in a second location on the meniscus (e.g., without removing it from the knee joint or having to reload) where the second suture leg is intended to be passed. The needle may then be passed through the tissue, and the angled region 1216 at the tip of the needle pushes the suture into the release pathway of the keyhole cutout region 1201, which is shown as an en enlarged circular region. The release pathway is typically an opening having a larger diameter than the enlarged distal end feature of the suture. The release pathway may also include a channel or ramp on the plate that guides the suture to the enlarged opening. This is illustrated in FIGS. 12G and 12H. FIG. 12H shows the needle just before it picks up the suture on its way back to the lower jaw. FIG. 12I shows the needle with the suture (and enlarged distal end feature 1205) held within the hook region of the needle.

As illustrated above, the needle (tissue penetrator) used for any of these procedures may be adapted to include a suture "pushing" region (hook region, etc.) and a suture "pulling region" (hook region). The suture pushing region is typically located more distally than the pulling region. In FIG. 12E, the needle has a distal-end adapted with a pushing region in which a notch is cut out of the distal end to hold the suture (and enlarged distal end region) as it pushes through the tissue. Proximally along the needle, a hook region, which is oriented so that the hook opening extends distally, is adapted for pulling the suture (and enlarged distal end region) back through the tissue towards the lower jaw. FIG. 12F illustrates another example of a needle in which the pushing region is not at the distal-most end, but is located proximal to the distal end. The needle includes a ramped region at the distal end.

Figure 13A:
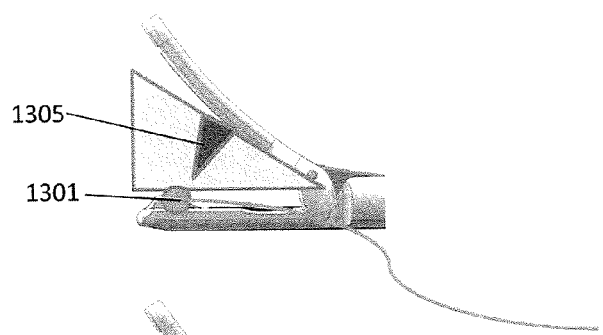
FIGS. 13A-13D illustrate operation of a suture passer as described in FIG. 12A-12I.
Figure 13B:
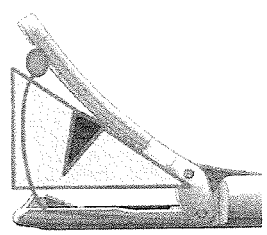
Figure 13C:
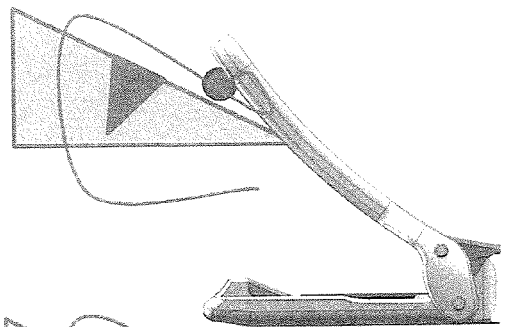
Figure 13D:
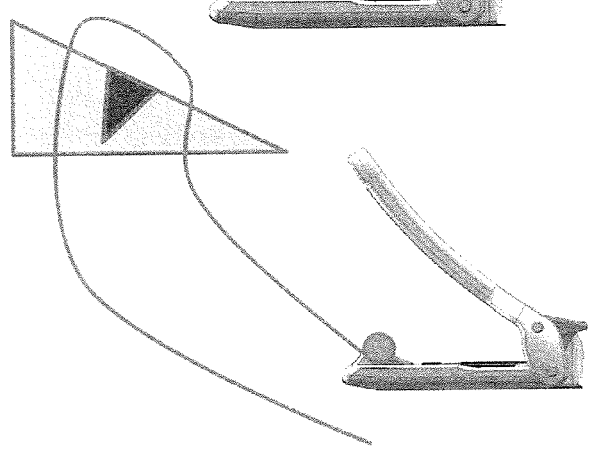

FIGS. 13A-13D show a profile view of the procedure using the keyhole cutout plate and the suture having an enlarged distal end feature. In FIG. 13A the suture passer is positioned around the meniscus, as previously described. Once the lower jaw is extended, preloaded with the suture with a knot (e.g., enlarged distal end region 1301, not shown to scale), the tissue penetrator may be extended, as shown in FIG. 13B, to push the suture through the meniscus on a first side of the tear in the meniscus 1305. The suture is retained in the keyhole cutout plate, and the suture passer may be repositioned on the meniscus, as shown in FIG. 13C (also not shown to scale). The needle may be extended back through on a second side of the tear (e.g., opposite from the first side), so that the knot is pushed by the returning needle into the large opening of the keyhole cutout plate (not shown) and captured by the pulling hook of the needle and withdrawn back through the tissue with the retracting needle, as shown in FIG. 13D. It should be understood that the terms "needle" and "tissue penetrator" are used interchangeably in this disclosure, though the broader "tissue penetrator" term applies.

Figure 14A:
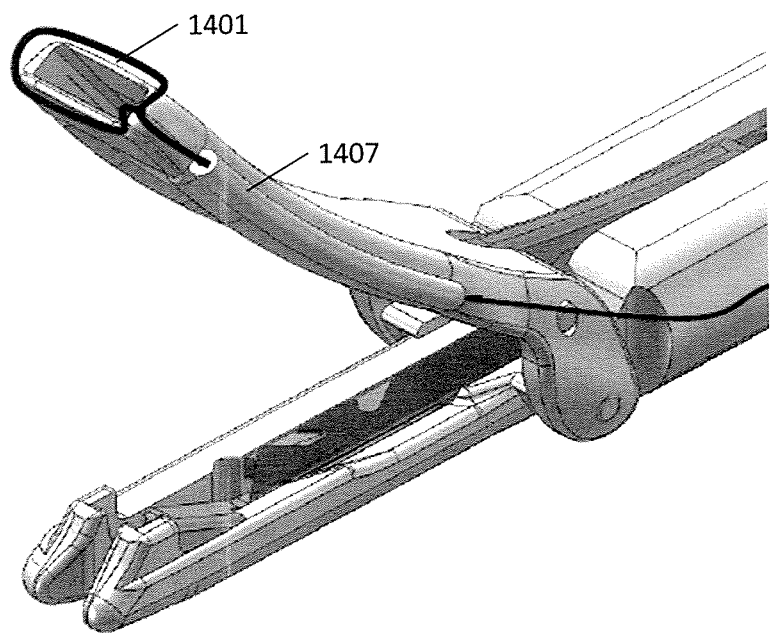
FIGS. 14A-14D illustrate another variation of a suture passer device including suture snaring (grasping) and release feature for passing a suture through a tissue to form a loop around the target tissue.
Figure 14B:
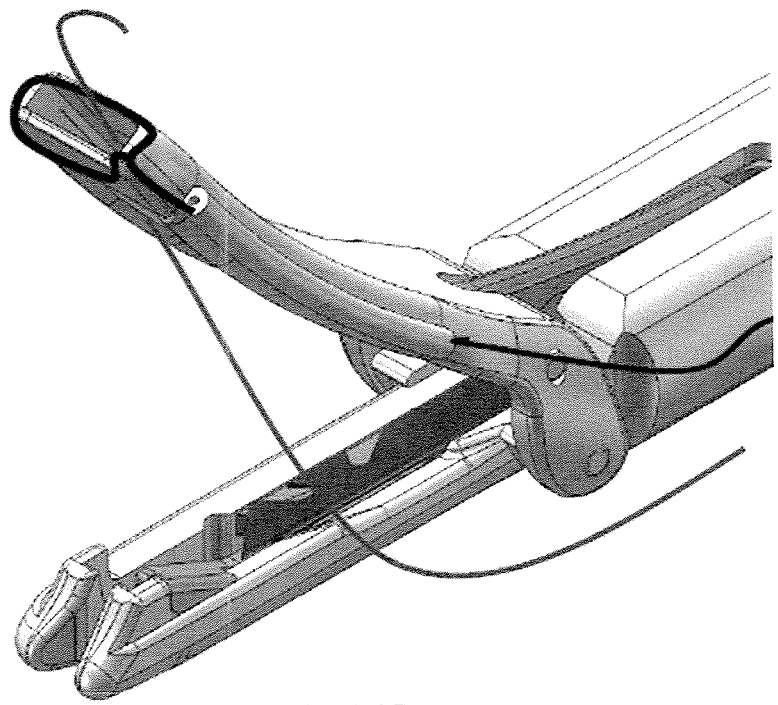
Figure 14C:
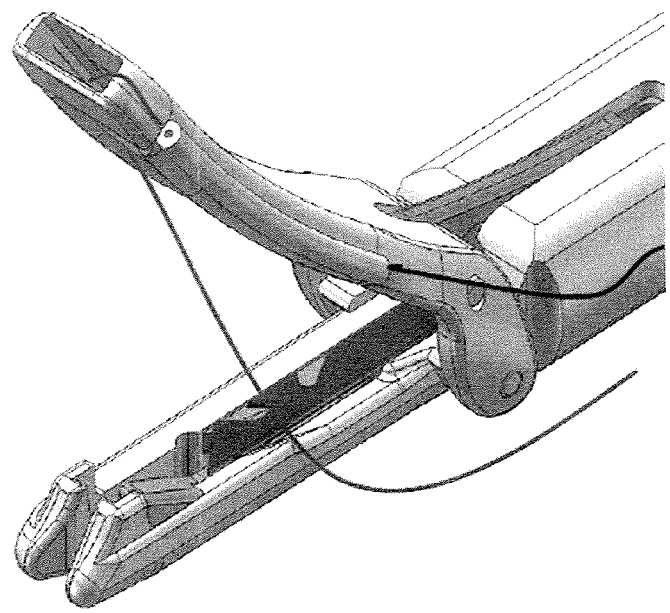
Figure 14D:
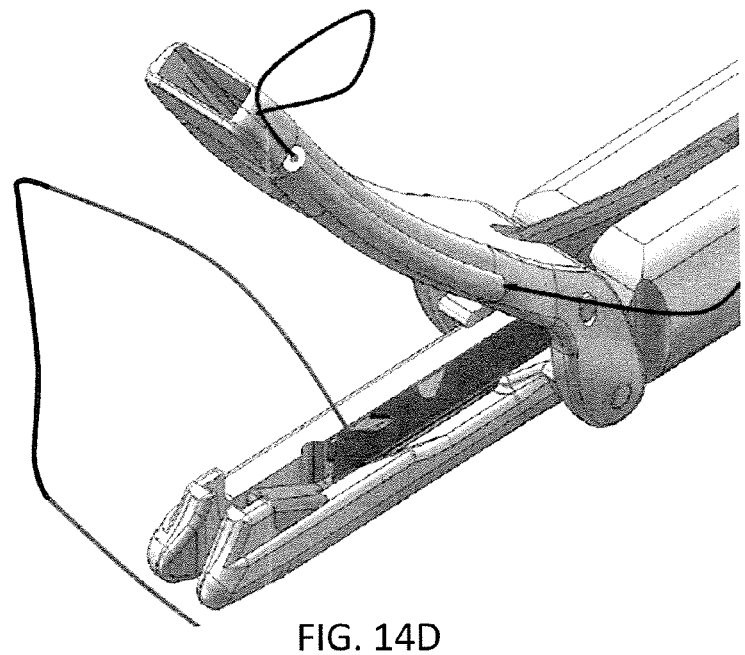

Another variation of a suture passer configured as a push/pull suture passer for forming a loop is shown in FIGS. 14A-14D. In the variation, the device includes a suture passer similar to those described above in FIGS. 5A-6D, but adapted to include a releasable snare. In FIG. 14A, the snare is shown having an open loop 1401 around the distal-facing opening of the upper jaw. The snare may be housed on the side of the device and retractable into this housing (e.g., snare guiding tube 1407). The opening of the snare loop 1401 may be positioned to accept the first leg of a suture. After the first leg is passed, the snare loop 1401 can be tightened and cinch the suture, thereby securing it to the device as it moves to the next position. The loop of the snare may be cinched by pulling the snare proximally so that the loop enters into the housing and closes over the suture, as described below. Once in position, the needle comes up again through tissue to retrieve the suture. The snare then release, and the needle may be pulled back through the tissue to the lower jaw. FIGS. 14B-14D illustrate these steps. In this variation, the snare may be a wire snare (e.g., nitinol, stainless steel, etc.), which runs through tubing alongside of the device. In FIG. 14B, the first leg of the suture has been passed through the tissue (not shown) and up through the snare opening. In FIG. 14C, the snare is pulled so that it retreats into the tunnel (snare guiding tube) along the side of the device, bringing the suture with it, and securing the suture in the closed loop, at least partially held within the narrow constrains of the snare guiding tube, while the device is repositioned. Finally, in FIG. 14D the snare loop may release its hold on the suture by extending the wire snare out of the snare guiding tube. The needle may be "fired" (sent across the tissue to the upper jaw) this time hooking the suture. Since the suture has been released by the snare, the suture is free to be pulled back through the tissue by the tissue penetrator and into the lower jaw.

Figure 15A:
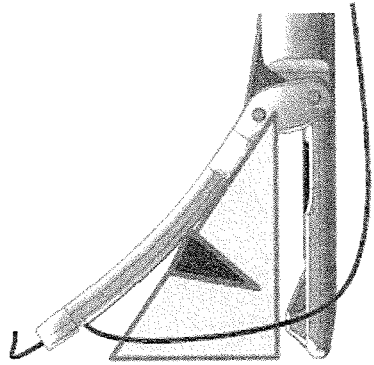
FIGS. 15A-15D illustrate operation of a suture passer as shown in FIGS. 14A-14D.
Figure 15B:
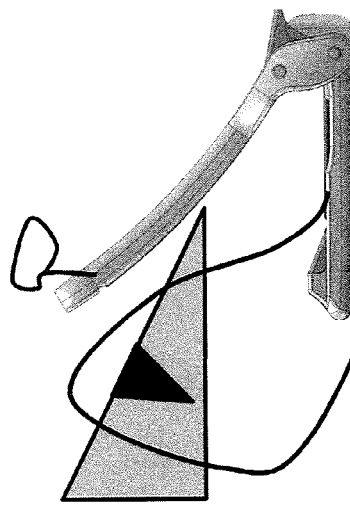
Figure 15C:
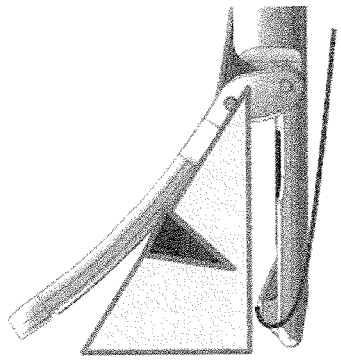
Figure 15D:
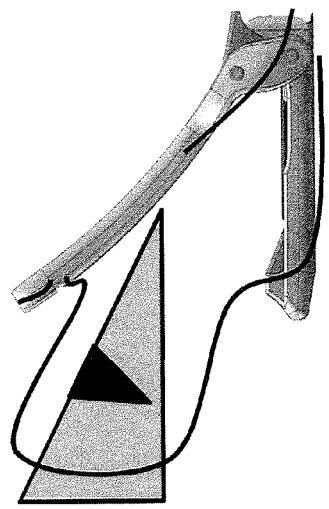

FIGS. 15A-15D show an illustration of this method applied to a meniscus. After positioning the suture passer around the meniscus (shown in FIG. 15A), the suture is pushed through the tissue to the upper jaw, where the suture passes through the snare opening (not shown) and the snare is pulled distally to capture the suture and hold it in the upper jaw while the suture passer is repositioned, as shown in FIG. 15C. Finally, the tissue penetrator is passed through the tissue again, the snare loop is released, and the tissue penetrator hooks and retracts the suture, withdrawing it back through the tissue to the lower jaw (FIG. 15D).

FIGS. 16A-16G illustrate another variation of a system and device for passing a loop of suture through the tissue. In this example, the suture is coupled at or near its distal end with an expandable capture element that makes it easier for the needle to recapture the end of the suture and pull it back through the tissue after it has already been passed through the tissue a first time. The capture element is typically expandable and collapsible, so that it present a small profile within the suture passer and/or within the tissue as it is being passed, but expands or opens to form a relatively large, and easy to capture profile once it has been passed through the tissue a first time. The suture passer may be adapted to hold and grab the expandable capture element. The capture element may be connected to a suture in any appropriate manner, including by tying, gluing, crimping, etc.

Any appropriate capture element may be used, including loops, baskets, coils, etc. The capture element may be flexible, and may be formed of metal, plastic, or the like. For example, in some variations the capture element is formed of a nitinol wire. A flexible loop or basket (e.g., made of nitinol), may be used to connect to the suture and be passed by the tissue penetrator which can grab the capture element in order to make a complete circle around a tear. The capture element, connected to the suture, would then shuttle a suture in its place through the tissue.

FIG. 16A shows an example of a suture passer that may be used, with the tissue penetrator extended. The tissue penetrator may be similar to that shown in FIGS. 5A-6D. In some variations the tissue penetrator is adapted to hold and release a capture element coupled to a suture in the lower jaw, and to allow the capture element to expand when released into the upper jaw. FIGS. 16B-16G are simplified illustrations of a method of forming a loop of suture around a tear in a meniscus (lateral tear 1609). For simplicity, the upper and lower jaws (which are extended around the meniscus) are not shown in FIGS. 16B-16G, although the suture, collapsible capture element and tissue penetrator are shown. In FIG. 16B, the suture passer is preloaded with the expandable capture element, and pushes it through the meniscus, from the inferior to the superior side. Once passed, the tissue penetrator retracts back through the meniscus to the lower jaw, and the collapsed capture element is free to expand. In FIGS. 16B-16G the capture element is a loop of wire that is biased open; as the tissue penetrator retracts back to the lower jaw, as shown in FIG. 16C, the loop expands open on the superior side of the meniscus. The capture element in this example is large enough to expand across the tear in the meniscus; the anatomical constraints of the tissue around the meniscus allow the expandable capture element to expand only on the superior surface in the predictable direction. Because the tissue penetrator pushed distally (up the superior surface of the meniscus) the loop expands in this direction. Re-orienting the suture passer may allow it to direct how and where the expandable capture element expands.

In FIG. 16D, the suture passer has been repositioned relative to the tear in the meniscus, so that the tissue penetrator may pass on the opposite side of the tear, as illustrated. The tissue penetrator extends out of the superior side of the meniscus and though the loop of the capture element. In FIG. 16E, the proximal end of the suture (which is attached distally to the capture element) is pulled proximally to tighten the loop around the tissue penetrator. The tissue penetrator is then retracted, pulling the capture element with it, as shown in FIG. 16F. As the capture element is drawn through the tissue, it again collapses. Once it has been withdrawn through the tissue, pulling the suture behind it, the capture element may be removed, and the ends of the suture secured, as shown in FIG. 16G.

In the example shown in FIGS. 16A-16G, a single tissue penetrator is shown placing the loop and then retrieving the loop. An alternative embodiment could have a lower jaw that contains two tissue penetrators (e.g., needles), one for placing the loop and another for retrieving the loop. Additionally, a third embodiment could contain two independent lower jaws, each containing its own needle. As in the second embodiment, one needle would place the loop and the other needle would retrieve the loop. By placing the needles in separate lower jaws, the two lower jaws could be independently actuated to allow the surgeon to adjust the distance between the two vertical legs of the stitch.

Figure 17A:
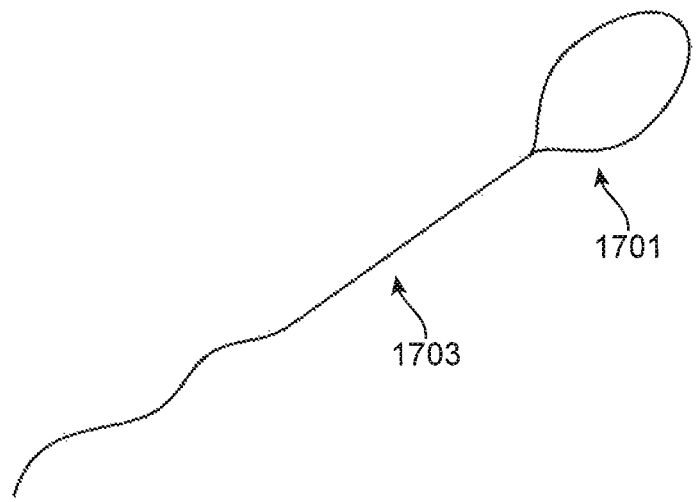
FIGS. 17A-17B illustrate variations of suture capture elements as described herein.
Figure 17B:
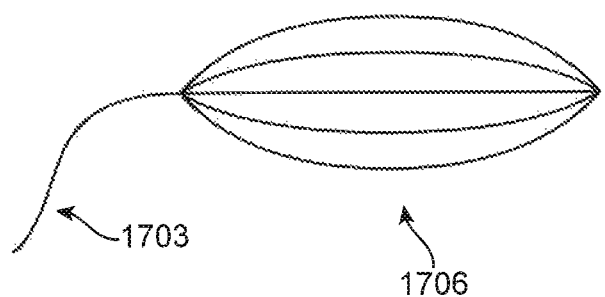

FIG. 17A shows one variation of an expandable capture element that is connected to a suture. In this example, the expandable capture element is configured as a nickel-titanium (e.g., nitinol) wire that forms a loop but is biased in the open configuration. The suture 1703 is connected to the loop 1701 (either directly or through a leader); for example, the suture may be tied to the flexible loop. FIG. 17B shows another variation of an expandable capture element, configured as a plurality of loops 1706 that are flexible but biased open (expanded). A suture 1703 may be affixed to the plurality of loops ("basket") 1706. The plurality of loops may help ensure that the tissue penetrator hook (e.g., pulling hook) catches the capture element; this feature may alleviate the need to cinch the suture (e.g., pull the suture proximally).

In some variations the expandable capture element is not extended substantially from the upper jaw member, but remains within the jaw member and is held by the upper jaw member after withdrawing the tissue penetrator so that when the tissue penetrator is again extended through the jaw, the tissue penetrator will pass through it, and the capture element can be pulled onto the tissue penetrator to engage with it so that it can be withdrawn back through the tissue.

Figure 18B:
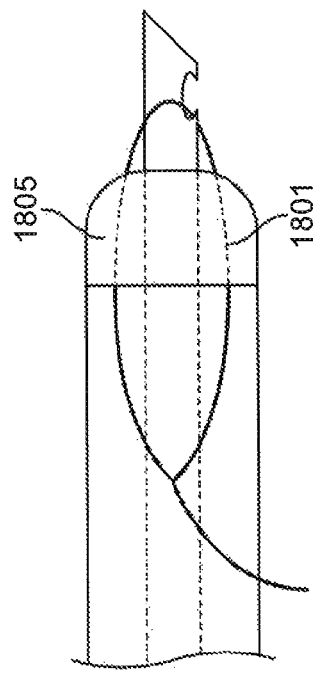
Figure 18D:
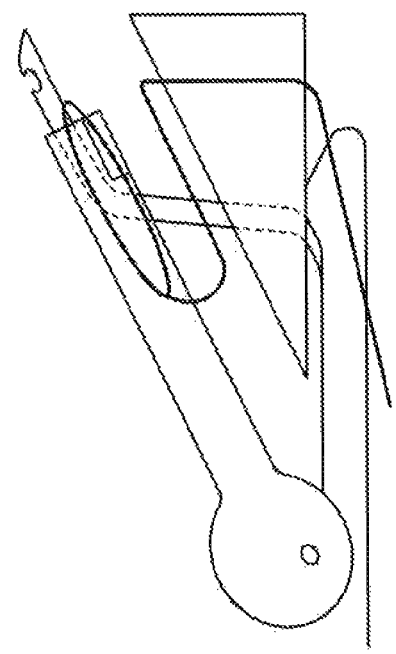
Figure 18A:
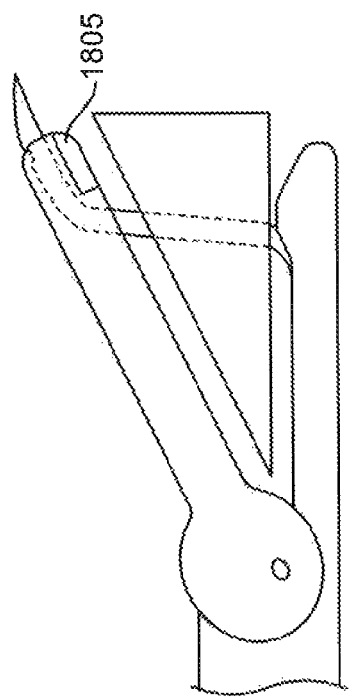
Figure 18C:
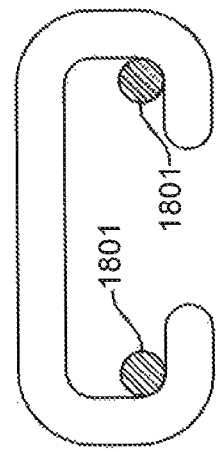

FIGS. 18A-18C illustrate this variation. In FIG. 18A, the tissue penetrator has an upper jaw member that includes a holding region 1805 for the capture element; in FIG. 18A, the holding region is defined on the underside of the upper jaw by a retaining plate 1805, as also illustrated in FIG. 18B. The nitinol loop 1801 is pushed by the needle so that the expandable capture element expands into the space under the upper jaw defined by the plate, as shown in FIG. 18B. The holding region may be defined by the upper jaw so that the capture element (e.g., loop) is held with an orientation that prevents the capture element from engaging with the needle when it is pushed fully distally. FIG. 18C shows a section through the holding region of the upper jaw, where a capture element 1801 is being held. After retracting the needle and repositioning the device, the needle/tissue penetrator can again be extended through the tissue and into the upper jaw, as shown in FIG. 18D. The needle may pass through the loop of the capture element held in the upper jaw. The suture may then be pulled proximally, reorienting the capture element and pulling it onto the needle so that it engages the needle and is pulled back through the tissue when the needle is withdrawn back though the tissue. This is illustrated in FIG. 18E (showing cinching of the loop of the capture element) and FIGS. 18F-18H, showing the capture element being withdrawn back to the lower jaw. In FIG. 18E, the suture 1803 is pulled to cinch the loop of the capture element onto the needle. In FIGS. 18F and 18G, the needle 1815 is shown capturing the loop of the capture element 1801. Finally, FIGS. 18H and 18I show the tissue penetrator completely withdrawn (holding the capture element) into the lower jaw (FIG. 18H), and the device being withdrawn from the tissue, as shown in FIG. 18I, which pulls the rest of the collapsed loop from the meniscus, and pulls the suture into position.

Figure 19A:
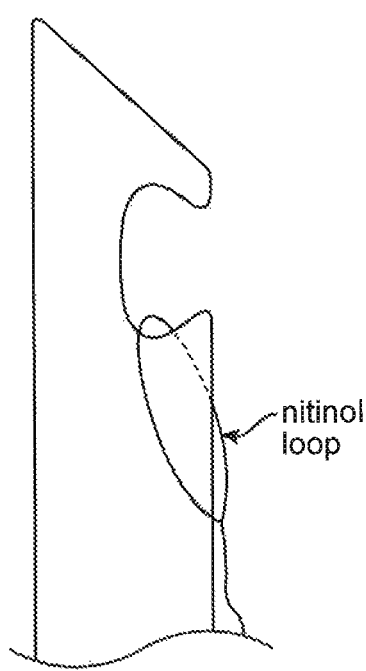
FIGS. 19A and 19B show alternative suture capture elements engaging a tissue penetrator.
Figure 19B:
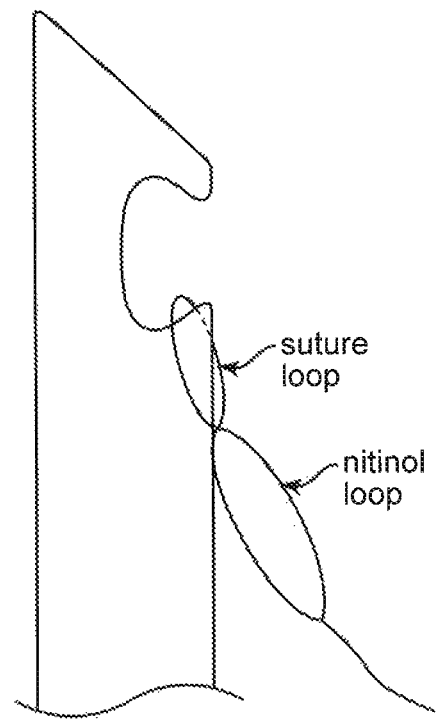

FIGS. 19A and 19B illustrate variations on the interaction between the capture element and the tissue penetrator. In FIG. 19A, the tissue penetrator couples with a loop of the capture element; thus the flexible loop can be preloaded onto the tissue penetrator before it is retracted into the lower jaw and primed to "fire" across the tissue. In some variations it may be beneficial to have the capture element be coupled to the tissue penetrator via a loop of suture material or other material that does not self-expand, such as the expandable capture element does. This may help with pre-loading the capture element onto the tissue penetrator, and may also help in reducing the force needed to pass the capturing element through the tissue. FIG. 19B illustrates one example in which a loop of suture is connected to the capture element that is also connected to a length of suture, as shown.

Enhancing Suturing Accuracy

Although the suture passers described herein may be used to pass sutures though tissue (and particularly meniscal tissue) having various thicknesses and dimensions by adjusting the bite (e.g., the angular distance between the upper and lower distal-facing jaws), adjusting the bite size may change the contact position of the needle/tissue penetrator as it extends from the lower jaw to the upper jaw. Note that in any of the variations described herein, the lower jaw may refer to either the first jaw or second jaw, as the orientation may be relative; similarly the upper jaw may refer to the opposite jaw, in any orientation. Although the devices describe herein are configured so that the devices tolerate changes in the contact point between the needle and the upper jaw, while still deflecting the needle distally as described above, it may be beneficial to know where on the upper jaw the needle will exit the tissue and contact the upper jaw. This may be referred to as targeting. It may be relatively less certain where the needle may exit the tissue when the bite size of the needle is smaller (e.g., when the jaws are more closed).

Figure 20B:
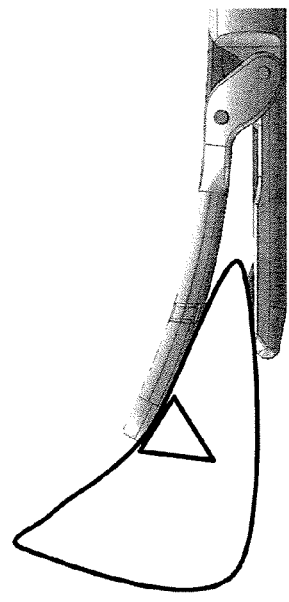
FIGS. 20A-20B illustrate clamping of tissue (e.g., meniscus tissue) between the jaws of a suture passer.
Figure 20A:
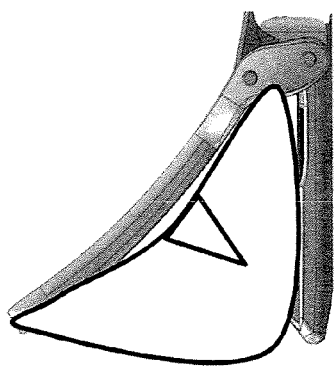

Described herein are methods and devices that allow the user to place a stitch in an intended location even when the jaws are relatively "closed" (e.g., small bite size), as when passing a suture in the more central regions of the meniscus. This uncertainty does not typically arise when placing a stitch at the periphery of the meniscus, when the bite size is relatively large, because the user can position the device as distal as it will go and blindly fire (see FIG. 20A). However, the when a stitch is placed on the middle of the meniscus or near the apex of the meniscus (see FIG. 20B), it is less certain where the needle may exit the tissue relative to the upper jaw. FIG. 20A shows the placement of a stitch near the periphery of a meniscus. A user can just push device past the tear and deliver stitch without worrying about accuracy of where the needle will contact the upper jaw. FIG. 20B shows a stitch near the apex of the meniscus. The surgeon is placing a stitch between the tear and the apex. However if the stitch is placed too close to the apex, the stitch won't grab enough tissue to be secure, too close to the tear and the stitch could be sent up through the tear. When the device is placed in a joint, such as the knee joint, the lower jaw may be completely covered by tissue, and the needle exit is invisible to the user. A stationary mark on the upper jaw is problematic because it may not predict where the needle with exit/hit; the needle may hit the upper jaw in different locations based on clamp height.

Described below are methods and device (e.g., adaptations to devices) that may be used to target stitch placement.

In some variations the lower (sliding) jaw is configured to move conjugally with the clamping of the upper jaw, so as to maintain an approximate relative striking distance between the tissue penetrator and the upper jaw when passing the tissue penetrator across the jaws.

Figure 21B:
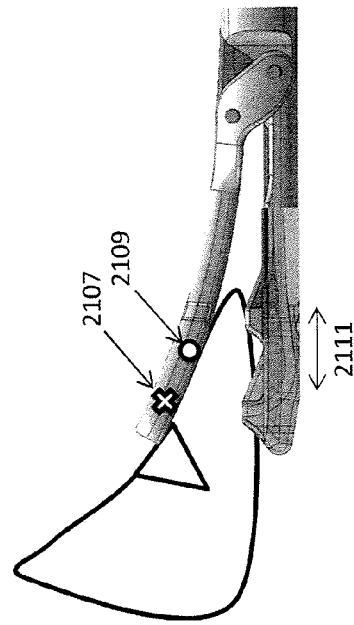
FIGS. 21A-21B illustrate the contact points of a suture passer with and without conjugate motion when clamping tissue between the jaws of the suture passer.
Figure 21A:
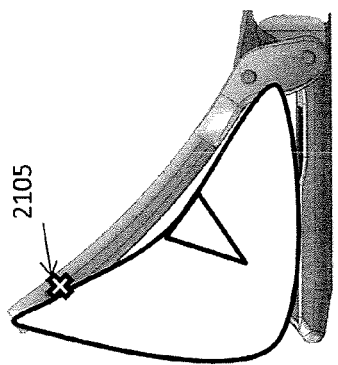

FIG. 21A shows a jaw moving though a large tissue thickness (e.g., a thick meniscus in this example). An exemplary "thick" tissue thickness may be 7.5 mm. At this size thickness, the needle will hit the upper jaw at a given location shown in FIG. 21A by the "X" 2105. Without conjugate motion between the upper and lower jaw (e.g., moving the lower jaw distally/proximally as the upper jaw bends to change the bite angle), the location of this contact point will vary, as illustrated by the more proximal contact point "o" 2109 in FIG. 21B. If, however, when the upper jaw clamps down, the lower jaw would move forward 2111, the contact point may be corrected to ensure that the needle hits the upper jaw in the same location, 2107. In this example, the lower jaw may move to the left 2111, relative to the shaft, to deliver the suture to the "X" target on the upper jaw 2107.

Thus, the suture passer may be configured as described above so that the lower jaw can be moved axially (distally/proximally relative to the elongate axis), both independently (to form the distal-facing opening, and also in conjugate motion when clamping/unclamping the upper jaw to change the bite angle of the suture passer.

In some variations, the movement of the upper jaw and the conjugate motion of the lower jaw can both be controlled by the clamp trigger (refer to FIGS. 5A-5B, for example). As the upper jaw clamps down, the axial distance of the "X" may move at a nonlinear rate distally. In order for the lower jaw to match that axial distance, it may also travel at the same rate. This can be accomplished by having the lower jaw motion controlled by a cam profile on the needle trigger. An example of such a cam profile is shown in FIG. 22.

Figure 22:
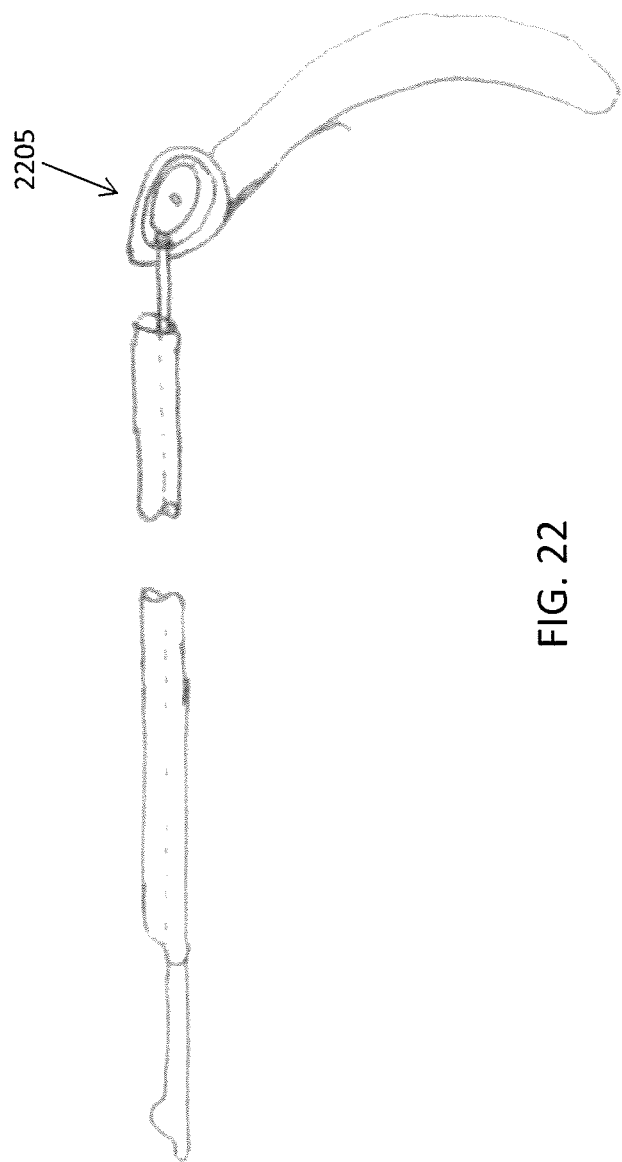
FIG. 22 illustrates a mechanism for achieving conjugate motion between an axial moveable lower jaw and a hinged/pivoting upper jaw.

In FIG. 22, the lower jaw include a cam follower 2205 that includes a camming surface that may also drive axial motion of the lower jaw when the upper jaw is moved. In this manner, motion of the upper jaw may be configured so that the axial position is adjusted based on the angle of the upper jaw with the elongate, long axis, of the device. The lower jaw may still be manually and independently axially movable to extend/retract axially. In some variations the lower jaw moved in conjugate motion with the upper jaw only when the lower jaw member is fully extended first (e.g., manually fully extended). Further, in some variations the conjugate motion between the upper jaw member and the lower jaw member may be turned "on" or "off" for the device.

Figure 23:
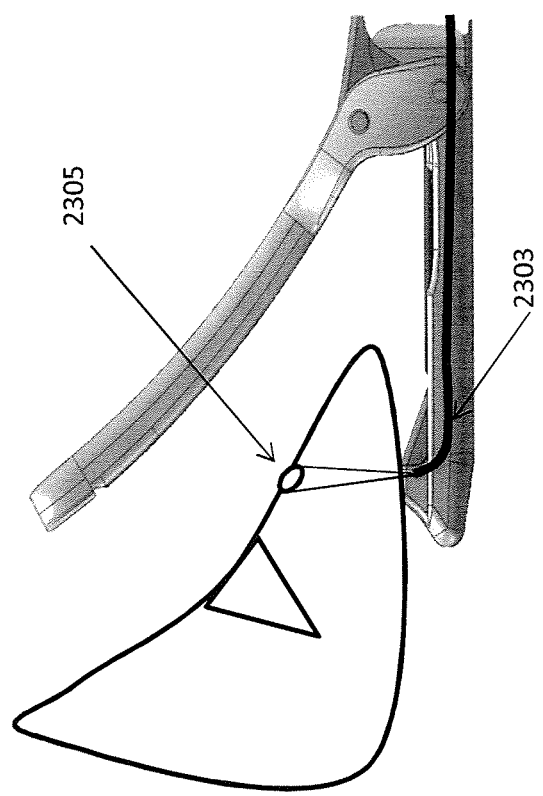
FIG. 23 illustrates operation of a suture passer device including a visual marking/notification element that projects light though the tissue to indicate the path that the needle (tissue penetrator) will take.

Also described herein are methods and devices for informing a user where the tissue penetrator may be passing through the tissue. As discussed above, it may be advantageous to provide an indicator to the operator of where the tissue penetrator (e.g. needle) will exit the tissue. In some variations the device may include an optical marking element (e.g., light) that indicates on the tissue and/or on the device, such as the upper jaw of the device, where the tissue penetrator will exit the tissue or where it will contact the upper jaw. FIG. 23 illustrates on variation of a device including an optical fiber 2303 extending with (and part of) the lower jaw that project a spot of light (e.g., visible or visualizable light) through the tissue. This light may be from an LED, laser, or other appropriate source. For example, a light source is placed on the lower jaw pointing toward the upper jaw to indicate where the needle will exit. In thin sections of tissue, if the light is strong enough, there should be a visible spot on top of the tissue that the user can use to place the stitch with confidence.

Tactile/Audible Feedback

Also described herein are devices configured to provide tactile and/or audible feedback to the user that the lower jaw and/or needle have been fully extended. For example, for certain suture passers, the grip force required to actuate the needle may be great enough that it is difficult for the user to feel the needle trigger's end of travel because the actuation force already placed high demands on the user's grip strength. Thus, it is hard for the user to detect that they are pushing up against something immovable, the travel limiter, because the force required to actuate the needle trigger feels may be great. In these cases, a suture passer device that provides an audible "click" or some other cue is helpful to the surgeon to ensure that he or she has fully actuated the device. For suture passers with slightly lower actuation forces, coupling the audible feedback with tactile feedback, whereby the surgeon feels a click or a detent just prior to the needle trigger hitting its travel limiter, could provide additional assurance to the user that he or she has properly completed actuation.

One method for providing both an audible and tactile cue is shown in FIG. 24A. FIG. 24A shows a cutaway view of the suture passer handle mechanism. In this example, the needle driver 2409 is rigidly attached to the needle (not shown). As the surgeon grips the needle trigger 2405, the needle driver 2409 translates forward. Because it is rigidly attached to the needle driver, the needle also translates forward as the needle trigger is gripped.

Figure 24B:
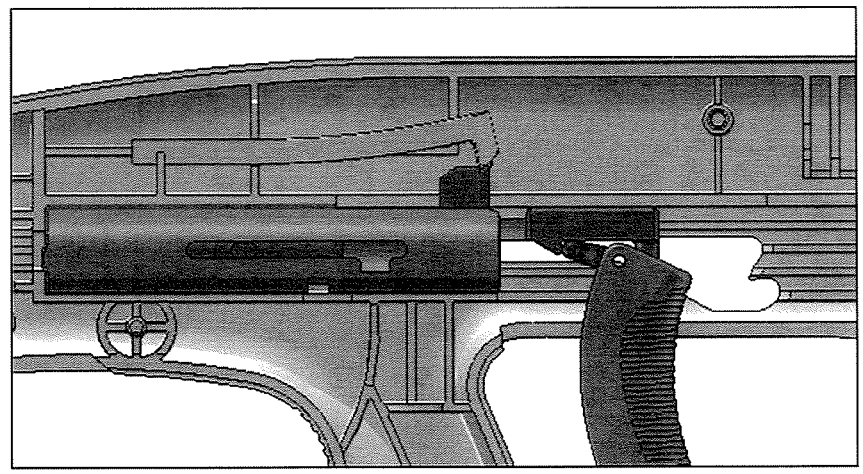
Figure 24C:
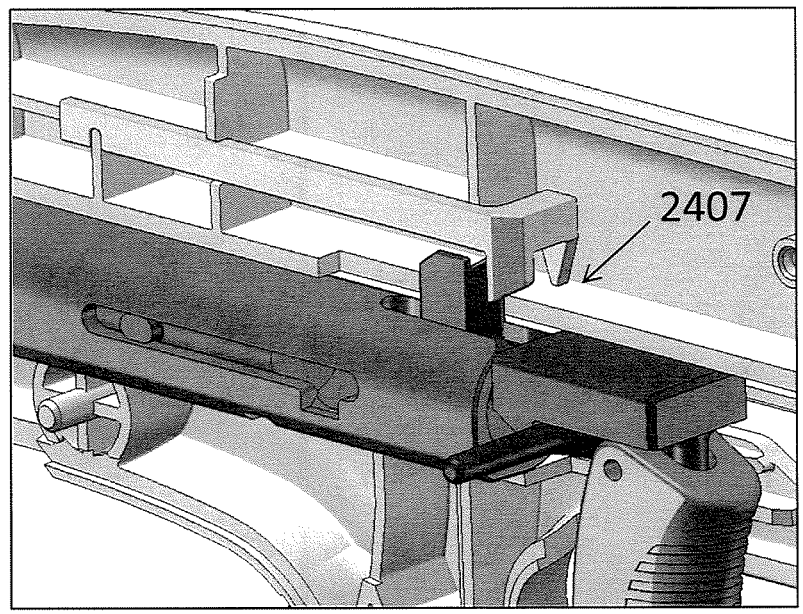

The needle driver contains a boss that, as it moves past a clicking element 2407, bends the Clicking Element upward as shown in FIG. 24B. Once the boss has moved distally past the interfering portion of the clicking element, the clicking element is free to snap back down where it impacts a feature 2415 on the handle (see FIG. 24C). This impact is enough to create an audible click that can also be felt in the user's hand.

Any other appropriate feedback actuator for providing audible and/or tactile feedback at or near the maximum extension of the needle and/or lower jaw may be used. The configuration described above in FIG. 24 is a mechanical feedback actuator; in some variations the system may use one or more optical encoders and a piezo or other electronic technique for providing feedback to the user (e.g., electrical feedback actuator).

Suture Cartridges

Figure 30:
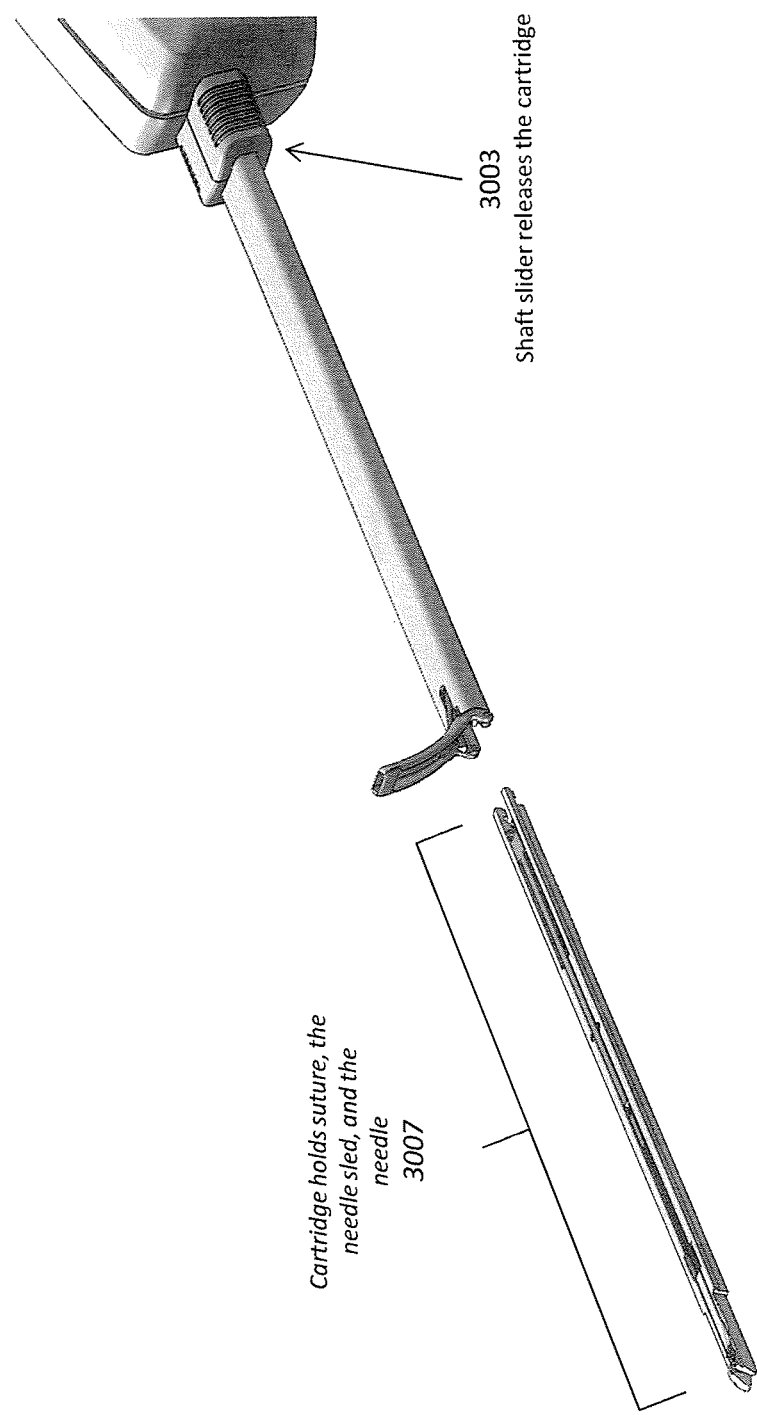
FIG. 30 shows a pre-loaded suture cartridge getting inserted into a suture passer.

Also described herein are suture passers having pre-loaded (with suture) axially slideable lower jaws. In some variations the cartridge is configured as a per stitch cartridge. The cartridge may contain a segment of pre-loaded suture which may or may not include a pre-tied knot and some portion of the distal end of the device. FIG. 30A shows an embodiment where the distal cartridge 3007 is comprised of the lower jaw component that contains the needle pathway, the needle, the needle sled (a connector that attaches the nitinol needle to a translatable element in the handle 3003), and a suture (not pictured). As mentioned above, the same features that allow separation of the lower jaw into a distal (needle path) and proximal (actuation control) portions that may connect/snap together may allow substantial reductions in the device height (e.g., the shaft height).

Figure 31:
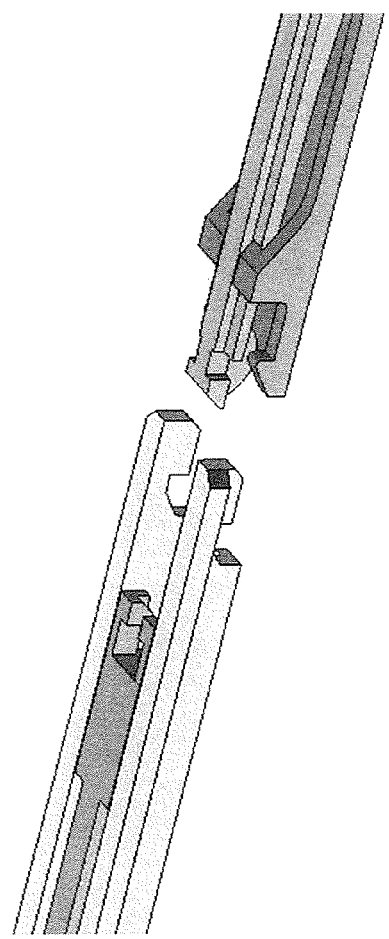
FIG. 31 shows the engagement region of the distal end component of the suture passer of FIG. 30 and the proximal end of the suture passer.

As mentioned, the proximal end of the cartridge may contain features that allow each of the members requiring actuation, the needle and the lower jaw, to click or snap into a corresponding actuator in the handle (See FIG. 31). An actuator on the handle can be activated by the user to disengage the connection features, facilitating removal of a used cartridge and readying the handle for loading a new cartridge.

Figure 32B:
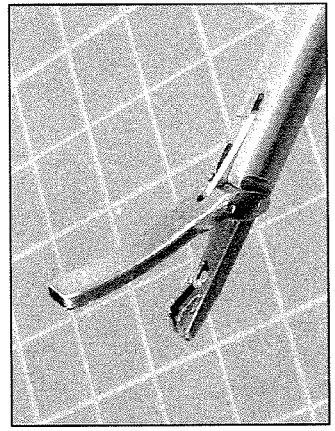
FIG. 32A-32B illustrate suture passers that have been pre-loaded with sutures from bottom and top perspective views, respectively.
Figure 32A:
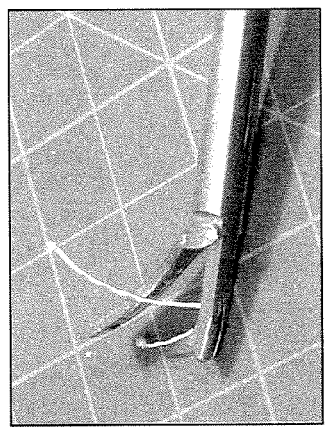

Sutures may be contained in the cartridge in a manner similar to that shown in FIGS. 32A-32B. The embodiment in FIGS. 32A-32B show knots at the ends of the suture, however, these could also be loops or some other feature that creates a shape that is larger than the base suture diameter so that it does not slip through the cut-out in the needle.

The advantages of a per stitch cartridge include preloading the suture into the cartridge so the surgeon or the scrub nurse do not have to deal with as much suture management in the sterile field, as well as keeping the suture housed within the lower jaw so that it cannot get pinched between the inferior surface of the device and the anterior horn of the meniscus or the tibia. Third, with both ends of the suture pre-loaded into the cartridge, the above architecture allows the surgeon to place both legs of the suture without removing the device from the joint. This eliminates the possibility of tissue bridging. Lastly, the handle is re-usable throughout the case.

Although the description above is broken into parts and includes specific examples of variations of suture passers, any of the features or elements described in any particular example or section may be incorporated into any of the other embodiments. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A suture passer for forming a loop of suture around a target tissue, the suture passer comprising:
    an elongate body extending distally and proximally along a long axis;
    a first jaw extending from a distal end region of the elongate body wherein the first jaw is bent or bendable at an angle relative to the long axis;
    a second jaw configured to slide axially along the long axis distally and proximally relative to the elongate body, further wherein the first jaw and the second jaw form a distal-facing opening when the second jaw is extended distally and wherein the second jaw is retractable proximally so that it does not form the distal-facing opening with the first jaw;
    a tissue penetrator configured to extend across the distal-facing opening between the first jaw and the second jaw to pass a suture there between; and
    a plate having a keyhole capture region, wherein the keyhole capture region comprises a capture pathway including a channel extending through the plate and a release pathway, wherein the capture pathway is connected to the release pathway by at least one bend, further wherein the plate is coupled to the first jaw so that it may receive a suture from the tissue penetrator extending from the second jaw.

2. The suture passer of claim 1, wherein the capture pathway comprise an opening mouth at an edge of the plate that tapers to a narrower channel before the release pathway.

3. The suture passer of claim 1, wherein the release pathway comprises an enlarged opening having a larger diameter than the region of the capture pathway adjacent to the release pathway.

4. The suture passer of claim 1, wherein the bend is configured to retain the suture immediately after it is passed into the keyhole capture region by the tissue penetrator.

5. The suture passer of claim 1, wherein the plate is configured as a suture stripper.

6. The suture passer of claim 1, further comprising a suture having an enlarged distal end region configured to be retained by the keyhole capture region, further wherein the diameter of the enlarged distal end region is greater than the diameter of the capture pathway but less than the diameter of a portion of the release pathway.

7. The suture passer of claim 6, wherein the enlarged distal end region comprises a knot.

8. A method of passing a loop of suture around a target tissue, the method comprising:

placing a first jaw of a suture passer adjacent to a first side of a target tissue, wherein the first jaw extends from a distal end of an elongate body of the suture passer;

extending a second jaw of a suture passer adjacent to a second side of the target tissue to form a distal-facing mouth with the first jaw, wherein the second jaw extends in a distal direction from the distal end of the elongate body of the suture passer;

extending a tissue penetrator between the first and second jaws of the distal facing mouth while pushing a capture member connected to a suture with the tissue penetrator;

retracting the tissue penetrator without the capture member or suture back between the first and second jaws of the distal facing mouth;

repositioning the first and second jaws relative to the target tissue;

extending the tissue penetrator between the first and second jaws of the distal facing mouth and capturing the capture member with the tissue penetrator; and retracting the tissue penetrator with the capture member back between the first and second jaws of the distal facing mouth.

9. The method of claim 8, wherein placing the first jaw comprises placing the first jaw adjacent to the target tissue with the second jaw retracted proximally so that the distal end of the second jaw is adjacent or proximal to the distal end of the elongate body of the suture passer.

10. The method of claim 8, wherein placing the first jaw comprises bending the first jaw relative to the elongate body.

11. The method of claim 8, wherein extending the tissue penetrator between the first and second jaws of the distal facing mouth while pushing the capture member comprises extending the tissue penetrator from the second jaw to the first jaw.

12. The method of claim 8, wherein extending the tissue penetrator between the first and second jaws of the distal facing mouth while pushing the capture member comprises pushing the capture member comprising a flexible loop wherein the suture is connected to the flexible loop.

13. The method of claim 8, wherein extending the tissue penetrator between the first and second jaws of the distal facing mouth while pushing the capture member comprises pushing the capture member comprising a plurality of flexible loops.

14. The method of claim 8, wherein extending the tissue penetrator between the first and second jaws of the distal facing mouth while pushing the capture member connected to the suture with the tissue penetrator comprises extending the capture member from a distal end of the first jaw member.

15. A suture passer device for passing a suture, the device comprising:

an elongate body extending distally and proximally along a long axis;

a first jaw extending from a distal end region of the elongate body wherein the first jaw is bendable at an angle relative to the long axis;

a second jaw having a sharp, tissue penetrating distal tip, wherein the second jaw is configured to be manually slid axially along the long axis distally and proximally relative to the elongate body, further wherein the first jaw and the second jaw form a distal-facing opening when the second jaw is extended distally and wherein the second jaw is retractable proximally so that it does not form the distal-facing opening with the first jaw;

a tissue penetrator configured to extend across the distal-facing opening between the first jaw and the second jaw to pass a suture there between; and a cam surface coupled to the second jaw and configured to move the second jaw axially in conjugate motion with bending of the first jaw member.

16. The device of claim 15, wherein the cam surface is coupled with a trigger control configured to change the bend angle of the first jaw relative to the long axis.

17. The device of claim 15, further comprising a control to engage or disengage the cam surface and engage or disengage the conjugate motion.

18. A suture passer device for passing a suture and providing feedback to the user, the device comprising:

an elongate body extending distally and proximally along a long axis;

a first jaw extending from a distal end region of the elongate body wherein the first jaw is bent or bendable at an angle relative to the long axis;

a second jaw having a sharp, tissue penetrating distal tip, wherein the second jaw is configured to slide axially along the long axis distally and proximally relative to the elongate body, further wherein the first jaw and the second jaw form a distal-facing opening when the second jaw is extended distally and wherein the second jaw is retractable proximally so that it does not form the distal-facing opening with the first jaw;

a tissue penetrator configured to extend across the distal-facing opening between the first jaw and the second jaw to pass a suture there between; and an audible feedback actuator configured to provide an audible signal when the tissue penetrator is fully extended across the distal-facing opening.

* * * * *